United States Patent
Lucas et al.

(10) Patent No.: US 8,614,257 B2
(45) Date of Patent: *Dec. 24, 2013

(54) PRODUCT RECYCLE LOOPS IN PROCESS FOR CONVERTING MUNICIPAL SOLID WASTE INTO ETHANOL

(75) Inventors: Stephen H. Lucas, Foristell, MO (US); Peter G. Tiverios, Anderson, SC (US); James R. Jones, Jr., Anderson, SC (US)

(73) Assignee: Fulcrum BioEnergy, Inc., Pleasanton, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/023,505

(22) Filed: Feb. 8, 2011

(65) Prior Publication Data

US 2011/0201700 A1    Aug. 18, 2011

Related U.S. Application Data

(60) Provisional application No. 61/302,516, filed on Feb. 8, 2010.

(51) Int. Cl.
*C07C 27/00* (2006.01)

(52) U.S. Cl.
USPC ........... 518/705; 518/700; 518/702; 518/703; 518/704

(58) Field of Classification Search
USPC ......................... 518/700, 702–705
See application file for complete search history.

(56) References Cited

U.S. PATENT DOCUMENTS

| | | |
|---|---|---|
| 5,666,891 A | 9/1997 | Titus et al. |
| 5,707,508 A | 1/1998 | Surma et al. |
| 5,756,957 A | 5/1998 | Titus et al. |
| 5,785,923 A | 7/1998 | Surma et al. |
| 5,798,497 A | 8/1998 | Titus et al. |
| 5,811,752 A | 9/1998 | Titus et al. |
| 5,847,353 A | 12/1998 | Titus et al. |
| 5,908,564 A | 6/1999 | Titus et al. |
| 6,018,471 A | 1/2000 | Titus et al. |
| 6,037,560 A | 3/2000 | Titus et al. |
| 6,215,678 B1 | 4/2001 | Titus et al. |
| 6,630,113 B1 | 10/2003 | Surma |
| 2007/0117195 A1 | 5/2007 | Warner et al. |
| 2010/0179315 A1* | 7/2010 | Medoff ..................... 536/123.13 |
| 2011/0201699 A1 | 8/2011 | Lucas |
| 2011/0201701 A1 | 8/2011 | Lucas |

FOREIGN PATENT DOCUMENTS

| | | |
|---|---|---|
| JP | 2006/334584 A | 12/2006 |
| WO | 2007/005954 A1 | 1/2007 |
| WO | 2009/009388 A2 | 1/2009 |
| WO | 2009/009389 A2 | 1/2009 |
| WO | 2009/114752 A1 | 9/2009 |

OTHER PUBLICATIONS

Phillips, S. et al., "Thermochemical Ethanol via Indirect Gasification and Mixed Alcohol Synthesis of Lignocellulosic Biomass," National Renewable Energy Laboratory, Technical Report NREL/TP-510-41168, Apr. 2007, 132 pages.
International Search Report and Written Opinion in PCT Application No. PCT/US2011/024108, mailed Oct. 20, 2011.

* cited by examiner

*Primary Examiner* — Jafar Parsa
(74) *Attorney, Agent, or Firm* — Nixon Peabody LLP

(57) ABSTRACT

Facilities and processes for generating ethanol from municipal solid waste (MSW) in an economical way via generating a syngas, passing the syngas through a catalytic synthesis reactor, separating fuel grade ethanol, extracting energy at particular strategic points, and recycling undesired byproducts.

7 Claims, 16 Drawing Sheets

PRODUCT RECYCLE LOOPS IN PROCESS FOR CONVERTING MUNICIPAL SOLID WASTE INTO ETHANOL

CROSS-REFERENCE TO RELATED APPLICATION

This application claims priority to U.S. Provisional Application No. 61/302,516, entitled "Process for Converting Municipal Solid Waste into Ethanol," filed 8 Feb. 2010, the content of which is incorporated herein by reference. This application is further related to U.S. patent application Ser. No. 13/023,497, titled "Processes For Recovering Waste Heat Form Gasification Systems For Converting Municipal Solid Waste Into Ethanol," and United States Utility patent application Ser. No. 10/023,510, titled "Gas Recycle Loops in Process For Converting Municipal Solid Waste Into Ethanol," both applications filed currently herewith, and the entire disclosures of both of which are hereby incorporated by reference.

TECHNICAL FIELD

This subject matter relates generally to processes, systems, and plants for converting municipal solid waste into ethanol.

BACKGROUND

Municipal solid waste (MSW) includes all solid materials disposed by municipalities. While some of this waste is recycled, the majority is typically dumped in landfills, where it decomposes over a period of decades or even centuries. It has long been recognized, however, that municipal solid waste contains organic materials that have energy content. If MSW is left untreated in landfills, this energy content drained slowly from the landfill by bacterial processes, which not only dissipate the concentrated energy, but also produce methane, which is a strong greenhouse gas. Some landfills have sought to collect this methane, which may be used for fuel; however, the conversion to methane takes place on long time scales, wastes much of the internal energy of the MSW, and is ineffective in recovering much of the available energy content of the MSW.

The earliest and most common method of recovering the energy from MSW is incineration. Incineration includes the combustion of MSW or refuse-derived fuel (RDF) to produce heat, which typically powers a turbine to produce electricity. Byproducts of incineration include fly ash, bottom ash, flue gases, and particulates. Fly ash and bottom ash are typically discarded in land fills. Flue gases and particulates can be scrubbed from the incineration flue stream prior to discharge into the atmosphere. However, effective removal of all harmful flue stream components can be prohibitively expensive.

Another method of recovering energy from MSW is pyrolysis, which involves heating the organic portions of the MSW, so that thermally unstable compounds are broken down and evaporate with other volatile components. These volatile components form a pyrolysis gas that includes tar, methane, aromatic hydrocarbons, steam, and carbon dioxide. The solid residue from pyrolysis process includes coke (residual carbon), which can then be burned or used for gasification. The byproducts of pyrolysis are often more stable and less toxic than incinerator ash.

A related method for recovering energy from MSW is gasification. This involves converting at least a fraction of the MSW into a syngas composed mainly of carbon monoxide carbon dioxide, and hydrogen. Gasification technology has existed for some two centuries. In the nineteenth century, the conversion of coal, often as a result of the coking process, into "town gas" provided a flammable mix of carbon monoxide (CO), methane ($CH_4$) and hydrogen ($H_2$) that was used for cooking, heating and lighting. During the twentieth century, more than a million biomass gasifiers produced CO and $H_2$ to meet transportation and mobilization needs during World Wars I and II. With the discovery of vast quantities of domestic natural gas after World War II, coal and biomass gasification was no longer cost-competitive and disappeared as an industry. Modern researchers have struggled to make gasification systems cost effective.

Sometimes, gasification has been applied directly to the MSW; in other cases, the MSW is first pyrolyzed, then subject to a secondary gasification process. Gasification of MSW generally includes a mechanical processing step that removes recyclables and other materials that have no energy content. Then, the processed feedstock is heated in a gasifier in the presence of a gasification agent (including at least some oxygen and possibly steam). Gasifiers may have a number of configurations. For example, fixed-bed gasifiers place the feedstock in a fixed bed, and then contact it with a stream of a gasification agent in either a counter-current ("up draft") or co-current ("down draft") manner. Gasifiers may also use fluidized bed reactors.

Another method of treating MSW is treatment in the presence of oxygen with a high-temperature plasma. Such systems may convert the MSW to syngas, leaving vitrified wastes and metals as byproduct.

After gasification plasma treatment, the resulting syngas is typically scrubbed to remove at least some of the particulates, acid gases, and soluble compounds. The scrubbing of syngas is much easier than scrubbing the flue gas of an incinerator because of the much lower volume of gases. The scrubbed syngas may be used to generate electricity by combusting the syngas in a boiler and using the steam to produce electricity, or by sending it to a combustion turbine that produces electricity in single or combined cycle operations. Alternatively, the syngas may be fed into a plant for the creation of synthetic fuels such as hydrocarbons or alcohols. Synthetic fuels have the advantage that they may be transported long distances and used to generate energy in a variety of devices at locations other than the syngas processing plant.

To create hydrocarbons as synthetic fuels, a common method for converting syngas into synthetic fuels is the catalytic Fischer-Tropsch process. This process produces a mixture of hydrocarbons. Another possibility is to create ethanol, methanol, n-propanol, and n-butanol, which may be incorporated into automotive fuels for use in existing automobiles. There are several known methods for creating ethanol and other higher alcohols from MSW, including acid hydrolysis and various bio-processes. However, these methods can often provide less favorable economics than desired. There are other catalytic processes that produce large yields of ethanol or other alcohols. For example, U.S. patent application Ser. No. 12/166,212 (filed Jul. 1, 2008, and incorporated by reference herein) describes a catalytic process to convert a syngas into a mixture of primarily methanol and ethanol. Because of tight energy constraints and the low cost of fossil fuels, it has been difficult to make these types of processes economically feasible. Creating ethanol from MSW efficiently is a difficult process that involves carefully managing feedstock quality, energy, syngas composition, syngas quality, product purification, and intermediate products. What is needed is an integrated process capable of converting MSW into ethanol economically, with low waste that can be disposed of safely and economically, and with low consumption of energy.

With the advent of higher gasoline prices, the development of alternative and synthetic fuels continues to attract significant interest. Synthetic fuels have the advantage that they may be transported long distances and may be used to generate energy at a location other than the syngas processing plant. However, because of tight energy constraints and the historical low cost of fossil fuels, it has been difficult to make synthetic fuel processes economically feasible. For example, creating ethanol and other alcohols from syngas efficiently is a difficult process that involves carefully managing energy, syngas, and other intermediate products. What is needed is a process capable of converting the waste materials such as MSW to syngas, and then syngas into alcohols economically and efficiently.

BRIEF SUMMARY

The present disclosure relates to facilities and methods for converting organic materials such as MSW into ethanol in an economical way. In various embodiments, the facilities may include a feedstock separator, configured to separate non-organic materials from a solid feedstock such as MSW, thereby creating a solid processed feedstock. The facilities may also have a gasification unit configured to generate a, usually very hot, from the processed feedstock. The heat from the hot syngas may be passed through a waste heat recovery system, which preferably comprises a heat exchanger or series of heat exchangers configured to generate superheated steam by cooling a stream comprising the primary syngas, thus outputting a cooled primary syngas stream. The facilities may preferably include a steam turbine and generator configured to use the superheated steam to generate electricity.

In some embodiments, the facilities may also include one or more syngas scrubbers configured to remove or neutralize one or more unwanted contaminants from the cooled primary syngas stream, such as particles, acid gases, catalyst poisons, etc., thereby to create a scrubbed syngas. To raise the pressure to a level appropriate for alcohol synthesis, the facilities may include a syngas compressor.

The facilities may include one or more alcohol synthesis reactors, comprising a catalyst, preferably arranged as one or more catalyst beds, in fluid communication with the syngas compressor. The reactor(s) may be configured to take at least a portion of the compressed gas stream from the syngas compressor as an input (recycle gases may optionally also be included within the stream entering the reactor or reactors) and produce an effluent. This effluent will preferably comprise unconverted syngas and a mixture of reaction products including alcohols and water. To recovery various recycle and product streams, the facilities may include a purification unit configured to separate at least a portion of the effluent into a number of streams comprising: an ethanol stream comprising primarily ethanol; a stream comprising primarily water; a methanol stream comprising primarily methanol; and a heavy alcohol stream comprising primarily propanol and heavier alcohols.

In one embodiment, the facility may recycle methanol generated in the purification unit back to the alcohol synthesis reactor(s). Methanol may for example be inserted prior to the reactor(s), between any two reactors in series, or within a space between two reactor beds or reaction zones within a single reactor, or some combination of the above.

In another embodiment, the facility may recycle a fusel oil stream to the gasification unit. The fusel oil stream may comprise a heavy alcohol stream separated in the purification unit, which also may optionally include methyl acetate which is also separated in the purification unit. In the gasification unit, the components of the fusel oil may be partially oxidized in some unit such as a thermal residence chamber (TRC), in order to convert at least some of the fusel oil components to a mixture comprising carbon monoxide and hydrogen, which may then be cycled as part of the syngas through the alcohol synthesis reactor(s).

Various additional embodiments, including additions and modifications to the above embodiments, are described herein.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted, based on this disclosure, in view of the common knowledge within this field.

In the drawings.

DETAILED DESCRIPTION

Figure 1:
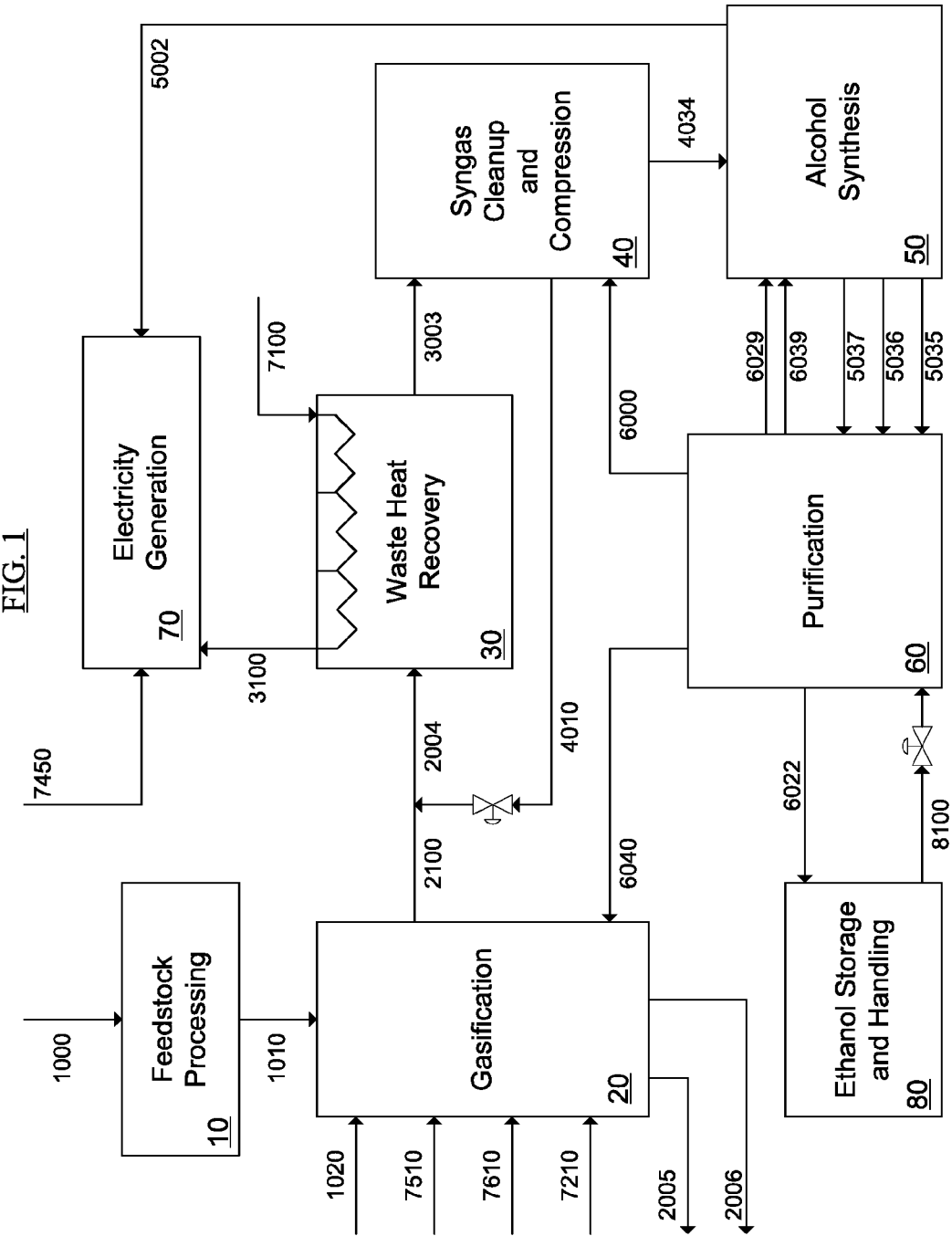
FIG. 1 shows one embodiment of an overall process for converting MSW into ethanol.

Various example embodiments of the present inventions are described herein in the context of converting municipal solid waste into ethanol along with possible co-products such as n-propanol and methanol.

Those of ordinary skill in the art will understand that the following detailed description is illustrative only and is not intended to be in any way limiting. Other embodiments of the present inventions will readily suggest themselves to such skilled persons having the benefit of this disclosure, in light of what is known in the relevant arts, the provision and operation of information systems for such use, and other related areas. Reference will now be made in detail to exemplary implementations of the present inventions as illustrated in the accompanying drawings.

In the interest of clarity, not all of the routine features of the exemplary implementations described herein are shown and described. It will of course, be appreciated that in the development of any such actual implementation, numerous implementation-specific decisions must be made in order to achieve the specific goals of the developer, such as compliance with regulatory, safety, social, environmental, health, and business-related constraints, and that these specific goals will vary from one implementation to another and from one developer to another. Moreover, it will be appreciated that such a developmental effort might be complex and time-consuming, but would nevertheless be a routine undertaking of engineering for those of ordinary skill in the art having the benefit of this disclosure.

Throughout the present disclosure, relevant terms are to be understood consistently with their typical meanings established in the relevant art. However, without limiting the scope of the present disclosure, further clarifications and descriptions are provided for relevant terms and concepts as set forth below:

The term stream as used herein means any fluid or solid moving or en route, directly or indirectly, from one location to another. A stream is still a stream even if it is temporarily stationary for any length of time. A conveyance means, means for conveying, conveyor, or pipe as used herein means any mechanism known in the art for conveying fluid or solid material directly or indirectly from one location to another (regardless of whether the material is presently moving within the mechanism), which may also be synonymous with the term stream. It will be understood that if this disclosure refers to a particular stream or conveyance means, this does not necessarily refer to a single pipe or other physical conveyance. There are many equivalent ways to convey fluid or solid material from one location to another, which may include the use of multiple fluid streams, conveyor belts, trucks or railcars, front-end loaders, or any other means of conveyance known in the art. All such streams or conveyance means are encompassed in this disclosure. In one non-limiting example, if any two locations are in fluid communication with each other, then it may be considered that there is a conveyance means between the two locations.

Reference to a portion of a stream or material refers to any portion of the stream or material, including the stream or material in its entirety. A portion of a stream or material may be mixed with other compositions of matter and the mixture will be considered to comprise the portion of the original stream or material.

The term mix or mixing means as used herein means any mechanism or process known in the art for mixing two compositions of matter. It may include two or more inlets meeting at a single location to allow two fluid streams to flow together into a single outlet, or it may include any type of mixer known in the art.

The term municipal solid waste (MSW) as used herein has the same meaning as the term is understood by one of skill in the art. An example of MSW is the solid waste that is obtained from the collection of municipal trash. In its raw form, MSW need not be entirely solid, as it may contain entrained or absorbed liquids, or liquids in containers or other enclosed spaces. One of skill in the art will understand that MSW will have a broad range of compositions, and that the source of MSW need not necessarily be from a municipality. For purposes of this disclosure, other organic waste materials such as organic industrial waste, construction and demolition wastes, medical wastes, and various biomass materials such as vegetative matter, may be equivalent to MSW.

The term unit as used herein means part of a system, and may for example comprise a unit operation, a system or group of unit operations, a plant, etc.

The term boiler feedwater (BFW) as used herein has the same meaning as the term is understood by one of skill in the art. Preferably, BFW may be prepared, stored in a tank, and forwarded to boilers or other steam generating units within an industrial process. Preferably, BFW may be conditioned to prevent scale, corrosion, or other fouling, or to prevent caustic embrittlement, sedimentation, priming and/or foaming.

The term plasma melter refers to a device comprising a chamber wherein a feedstock is exposed to a plasma arc in conjunction with or without a joule-heating element. Although many plasma units are possible, preferably, various embodiments of the plasma melter technology provided by InEnTec LLC may be used. These embodiments are described, for example, in U.S. Pat. No. 5,666,891 and its related family of patents (including, without limitation, U.S. Pat. Nos. 5,707,508, 5,756,957, 5,785,923, 5,798,497, 5,811,752, 5,847,353, 5,908,564, 6,018,471, 6,037,560, 6,215,678, and 6,630,113), the disclosures of which are incorporated herein by reference. Reference herein to a plasma melter may refer to any of these technologies described in these patents, or their equivalents, or modifications that would be obvious to one of skill in the art.

The term thermal residence chamber (TRC) refers to a chamber that is configured to provide additional residence time, in the presence of oxygen, to thermally crack hydrocarbons present in the syngas, and allow gasification and other gas phase reactions to go to completion or near completion. Various example embodiments are described in the InEnTec LLC patents listed above.

The terms syngas generation unit or gasification unit refer to a unit or set of units that generate syngas, which might for example include, without limitation, gasifers, plasma melters, plasma arcs, plasma torches, combinations of gasifiers and plasma melters, steam reformers, pyrolysis reactors including for example slow pyrolysis or fast pyrolysis units, reformers, catalytic oxidizers, thermal oxidizers, reducing thermal oxidizers, and combinations of the above, possibly in combination with one or more TRCs. Each of the above components may operate in either a batch or continuous process.

The term syngas (synthesis gas) as used herein has the same meaning as the term is used by one of skill in the art. For example, syngas may comprise a combination of carbon monoxide, hydrogen, and possibly other components such as, without limitation, water vapor, sulfur- or nitrogen-containing gases, carbon dioxide, methane, hydrocarbons, acid gases, and particulates.

The term separator as used herein refers to any process unit known in the art for performing a separation process, including without limitation distillation columns, membrane separation systems, ion exchange adsorption systems, thermal adsorption, pressure swing adsorption, molecular sieves, flash drums, absorption or adsorption columns, wet scrubbers, Venturi scrubbers, centrifuges, chromatographs, or crystallizers. Separators may separate fluids or solids, or fluids from solids.

The term in fluid communication with as used herein includes without limitation both direct and indirect fluid communication, such as, for example, through an intermediate process unit.

The term heat exchanger as used herein includes without limitation any heat exchanger or heat exchange device known in the art, and more broadly, any device which raises the enthalpy or internal energy of a first composition of matter, decreases the enthalpy or internal energy of a second composition of matter, and transfers heat from the second composition of matter to the first composition of matter. Various heat exchange means are disclosed herein, all of which are encompassed within this term. The term also includes combinations or series of multiple heat exchange means. It includes, without limitation, shell and tube heat exchangers, air or "fin-fan" coolers, refrigeration units, chillers, cooling towers, steam generators, boilers, plate heat exchangers, adiabatic wheel heat exchangers, plate fin heat exchangers, fluid heat exchangers, waste heat recovery units of any kind, or phase change heat exchangers of any kind They may operate in a countercurrent, parallel, crosscurrent configuration, or any other flow configuration, and may involve separation of two fluids or direct contact between two fluids, or the use of an intermediate fluid (such as water, hot oil, molten salt, etc.) to transfer heat from one fluid to another.

The term compressor as used herein includes anything that is understood as a compressor in the normal sense of that term. In general, however, the term includes any device that raises a fluid from a first pressure to a second, higher pressure, either adiabatically or non-adiabatically. It may include any kind of compressor or pump, including without limitation, centrifugal or axial, or positive displacement (such as reciprocating, diaphragm, or rotary gear). The term may also include one or more stages of a multi-stage compressor. The term compressor used in the singular may also refer to multiple compressors arranged in series and/or parallel.

The present disclosure describes various embodiments of a MSW to alcohol process that may include some or all of the following elements: a gasification unit, a waste heat recovery unit, a syngas cleanup and compression unit, an alcohol synthesis unit preferably containing one or more catalytic alcohol synthesis reactors, a carbon dioxide removal unit, and purification unit for recovering and purifying ethanol from a reactor effluent. An embodiment of the disclosure generates electricity from syngas and/or steam generated form waste heat. An embodiment may recycle methanol to the reactor, and may partially oxidize higher alcohols and methyl acetate as fusel oils in a gasification unit.

The creation of ethanol from MSW in this way has significant economic and environmental advantages. It reduces dependence on foreign oil, provides an energy efficient system with a very low emissions profile, reduces MSW entering landfills (thus dramatically reducing harmful methane gas emissions from landfills, and mitigating the need for new or expanded landfills), reduces by displacement other greenhouse gases associated with the use of petroleum and coal derived fuel products, and creates new green jobs.

FIG. 1 shows one embodiment of an overall process for converting MSW into ethanol. First, MSW feedstock 1000 containing a heterogeneous variety of municipal waste materials, or other waste materials or biomass of a similar nature containing organic material (for example, various embodiments may use wood, bio-mass, straw, switch grass, or construction and demolition wastes), may be processed in a feedstock processing unit 10. In this unit, the waste material may be sized, separated, and processed to remove materials that are not useful in the process, or which might reduce its efficiency. For example, one might want to remove metals, inorganic materials, and wet materials such as food waste or agricultural products. Such materials may, for example, be recycled or sent to a landfill or dried and sent to the gasification unit along with other materials. Qualifying post-recycled or post-sorted feedstock 1010 may be sent to a gasification unit 20. The gasification unit may comprise one or more syngas generation units. In one embodiment of the gasification unit, glass cullet 1020 may be added to facilitate the vitrification of inorganic non-metallic material, particularly if the gasification system includes a plasma melter. Oxygen 7510 and steam preferably generated from boiler feedwater (BFW) 7210 may be reacted with the feedstock 1010 to produce syngas 2100. A nitrogen stream 7610 may be used as a purge material, especially during start-up or shut-down. The gasification system may be configured, and conditions provided, so that at least the following gasification reaction Occurs:

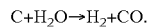
$$C+H_2O \rightarrow H_2+CO.$$

Simultaneously, conditions may preferably be provided so that the following reversible "water shift" reaction reaches an equilibrium state determined mainly by the temperature of the gasifier, the pressure preferably being near atmospheric:

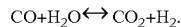
$$CO+H_2O \leftrightarrow CO_2+H_2.$$

Byproducts of the gasification unit 20 may include a glassified vitrate 2005, which may preferably be sent to a landfill, and/or a metal 2006 which may preferably be recycled. For safety and control purposes, the system may preferably be designed so that syngas 2100 may be quenched if necessary or desired by relatively low temperature syngas 4010, which is preferably recycled from a location downstream of the waste heat recovery system 30, preferably from syngas cleanup and compression unit 40. In another embodiment, syngas 2100 may be quenched using a recycle stream of methanol, preferably methanol from purification unit 60. During this quenching process, methanol may be dissociated to hydrogen and carbon monoxide. In another embodiment, syngas 2100 may be quenched by water.

Syngas 2004, which is either syngas 2100 or a mixture of mixture of syngas 2100 and 4010, may be passed through waste heat recovery system 30, which in a preferred embodiment comprises one or more waste heat steam generators (WHSG) to cool the syngas 2004 while generating steam 3100 from BFW 7100. The steam 3100, preferably in addition to steam from other parts of the process as well, may be sent to an electricity generation unit 70 preferably comprising a steam turbine.

Relatively cool syngas 3003 may be quenched with water in a direct contact Venturi scrubber and may be passed through syngas cleanup and compression unit 40, where it may be cleaned of undesirable contaminants such as, for example, particles, acids and acid gases, mercury, lead, and other volatile metals, and compressed to a high pressure (syngas 4034). A relatively low-pressure syngas recycle stream 4010 may preferably be used, if necessary or desired, to quench the hot syngas stream 2100. Such quenching may be appropriate, for example, to keep the syngas below the eutectic range of various minerals that may be present in the fly ash so that those minerals will not coat boiler tubes within the waste heat recovery unit 30. Preferably, the temperature of syngas stream 2004 entering the waste heat recovery unit 30 will be in the range of about 649 to about 760° C. (about 1200 to about 1400° F.). By recirculating the cool syngas to quench the hot syngas, the energy content of the syngas entering unit 30 may be preserved by transferring the heat to the recycled gas stream rather than to an alternative stream such as water. However, the hot syngas stream 2100 may also be quenched by water in an alternative embodiment.

High pressure syngas 4034 may be fed to the inlet to the alcohol synthesis unit 50, which may produce one or more streams 5035 (liquid) and/or 5036 (gas) comprising mixed alcohols, and water stream 5037 to be fed to a lower pressure purification unit 60. Preferably, at least part of the syngas (5002) prior to compression may be sent to electricity generation unit 70 which may contain a combustion turbine for burning syngas purge gas 5002 from the alcohol synthesis recycle loop, and/or natural gas 7450 in air to produce electricity.

In purification unit 60, syngas may be vented from the mixed alcohol stream and preferably recycled (syngas 6000) to the syngas cleanup and compression unit 40. Water may be separated from one or more of the mixed alcohols and some or all of it may preferably be recycled (stream 6029) to the alcohol synthesis unit where it may be used to absorb mixed alcohols from the reactor effluent gas. In addition purification unit 60 may separate methanol 6039, which may be recycled to the alcohol synthesis unit 50 to be dissociated into carbon monoxide and hydrogen, and eventually converted to ethanol or may have an additional carbon atom inserted into the molecule along with additional hydrogen atoms to form ethanol. The purification unit may separate and collect heavy alcohols (preferably heavier than ethanol) as fusel oil 6040 for recycling to the gasification unit 20. The resulting product ethanol 6022 may be sent to an ethanol storage and handling unit 80. If the ethanol is off-specification, it may preferably be recycled back (8010) to a location within the purification unit 60 and re-purified.

The ethanol storage and handling unit 80 may comprise any number of storage tanks, and facilities for testing, loading, and shipping ethanol to its final destination. It may also include facilities for denaturing the ethanol such as by the addition of gasoline or other additives. Unit 80 may also contain a pump for recycling any off-specification ethanol 8100 back to a point upstream in the process where it can be re-purified.

Feedstock Processing

There may be several embodiments of a feedstock processing unit 10. For example, without limitation, the unit may process wood bio-mass, straw, switch grass, and other like biomass materials. Construction and demolition wastes may also be processed. Preferably, the waste will have a high concentration of organic material, so that the vast majority of non-organic materials may preferably be removed in unit 10 with relatively minimal processing effort. In a particular preferred embodiment, the MSW feedstock 1000 comprises the organic component of MSW derived from the residual materials remaining after recycling operations are performed by material recovery facilities. This described embodiment may also be applicable to other types of feedstock containing organic materials, such as biomass or construction and demolition materials. Feedstock may be drawn from solid waste material recovery facilities (MRFs). These facilities receive collected MSW, then sort and process the waste to remove commercially recyclable materials. The recyclable materials may either be separated by the customers themselves—typically at homes and offices—or by the MRFs.

The feedstock may be delivered to the feedstock processing unit 10 by tipper-type fixed floor transfer trailers or construction roll-off trailers. The MSW may be shredded to reduce the maximum material size, preferably to less than about 4 inches, and processed through various solids handling equipment to remove the material that is not suitable for gasification.

In a particularly preferred embodiment, feedstock trucks may be weighed with a truck scale as they enter and exit the site to accurately determine the quantity of MSW delivered. Delivery trucks may be of any capacity, but may preferably have an MSW capacity of about 23 to about 24 tons. In the preferred embodiment of this disclosure, approximately 650 tons of MSW may be delivered per day. However, if a facility is designed to process more or less than this amount, one of skill in the art will know how to scale up the quantities, rates, and sizes of equipment to efficiently handle that capacity.

In one embodiment, the feedstock may be deposited on a receiving floor and examined. Personnel may remove material volumes of food waste and other wet organics and send those materials to composting facilities, or the process of removing such wet organics may be removed by automated means known in the art. Personnel may also identify and remove oversized, prohibited, or undesirable objects while on the receiving floor, or these objects may be removed by automated means known in the art. The remaining carbonaceous material will preferably be relatively dry, consisting of preferably 15 to 25% moisture.

A hydraulic-operated feedstock trailer tipper may be used to unload the MSW into a pile on the floor of a building housing feedstock processing facilities. The building may preferably be sized to allow for the storage of about one day of MSW. Undesirable material may be removed from the MSW pile using a front-end loader and placed in a reject dumpster for return to the landfill.

A front-end loader may be used to load the MSW into a processing feed bin. This bin may preferably be sized to provide about 10 minutes of MSW feed to the preparation system. A moving floor in the bin may transfer the raw feedstock to a scalping apron conveyor that meters the feedstock and deposits the feedstock on a flat conveyor. The flat conveyor may provide for a "pre-sort" station that permits the manual removal of unwanted material (such as structural steel, propane bottles and PVC) that is readily spotted by operating personnel. The feedstock then falls directly into a primary shredder. This shredder may reduce the size of the feedstock constituents to a maximum dimension of preferably about 8 inches in any direction. The shredded feedstock may then be conveyed to a primary debris roll screen, where material smaller than preferably about 5.08 cm or 2 inches (the "2 inch minus processing train," discussed below) may be removed from the main feedstock stream.

Preferably, the main feedstock material between about 5.08 and 20.32 cm (about 2 and 8 inches) in size leaving the primary debris roll screen may be conveyed to a primary single drum separator where circulating air may be utilized to separate the "light" feedstock material from "heavy" residue material such as rocks and concrete. The residue material may be transferred to a residue collection conveyer and then moved to transfer trucks for disposal. The main feedstock stream from the drum separator may be conveyed to a primary cross belt magnet to remove the ferrous material in the stream. The ferrous material collected by the magnet may then be conveyed to dedicated rollaway containers.

The main feedstock stream that passes under the primary cross belt magnet may then be combined with dry organic material (preferably in the range of about 1.27 cm to 5.08 cm or ½ to 2 inches in size) from the 2 inch minus processing train on a conveyor. The combined stream may then be dropped onto the inlet conveyor for an eddy current separator where non-ferrous metals (mainly aluminum) may be removed from the feedstock. The non-ferrous material may be conveyed to dedicated rollaway containers.

The feedstock from the eddy current separator may be dropped onto an inlet conveyor for an optical sorter where PVC material may be identified and separated from the feedstock using infrared detectors and blasts of high-speed air. The PVC material may be transferred to a residue collection conveyer for disposal with the rest of the residue. The feedstock from the optical sorter may be flowed under a tertiary cross belt magnet for the final removal of ferrous material in the stream. The ferrous material collected by the magnet may be further conveyed to dedicated rollaway containers.

After passing under the tertiary cross belt magnet, the feedstock (now preferably relatively free of heavy inert material, ferrous and non-ferrous metals, wet organic material and PVC) may be dropped onto a secondary debris roll screen. This secondary screen may preferably separate material smaller than preferably about 10.16 cm (about 4 inches) from the larger material and deposit the smaller material on a small material conveyor. The larger material may leave the secondary screen and fall into a secondary shredder where the size of the larger feedstock constituents may be reduced to a maximum dimension of preferably about 4 inches in any direction. The freshly shredded material may be combined with the material from the small material conveyor that bypassed the shredder. The combined feedstock, preferably consisting of constituents no larger than about 10.16 cm (about 4 inches), may be conveyed into a feedstock storage building and deposited on the building floor or bailed for open storage.

Two inch minus processing train from the primary debris roll screen may be deposited onto a primary vibratory screen where preferably about 0.95 cm (about ⅜ inch) and smaller "gritty material" (i.e., rock, glass, metal, dirt, concrete, etc.) may be separated from the stream. The approximately 0.95 cm (approximately ⅜ inch) and smaller material may be transferred to a residue collection conveyer for disposal with the rest of the residue. The remaining material (approximately 1.27 to 5.08 cm or ½" to 2") may be transferred to a secondary single drum separator. The drum separator may preferably utilize circulating air to separate the organic material from the heavier inert material. The heavy inert material from the drum separator may be transferred to a residue collection conveyer for eventual disposal. The primarily organic material from the drum separator may drop onto a conveyor that passes the material under a secondary cross belt magnet to remove the ferrous material in the stream. The ferrous material collected by the magnet may be further conveyed to dedicated rollaway containers. The remaining feedstock may then be dropped onto the inlet conveyor for an air classification unit to separate the wet (heavy) material from the dry (light) organic material.

The wet organic material may be sent to a separate system where it may be dried and returned to the feedstock system upstream of the gasifiers. Alternatively, the wet material may be discarded. The dry organic material from the air classification unit may be transferred, preferably pneumatically, to a rotary air separator, where the dry organic material separates from the transport air stream and is conveyed to join the main feedstock stream upstream of the eddy current separator (discussed above).

The feedstock storage building may preferably be sized to store about two days of gasifier feed (approximately 1000 tons in the preferred embodiment of this disclosure). A front-end loader may be used to place the feedstock in storage piles and to load the processed feedstock into a feedstock feed hopper. This feed hopper is preferably sized to provide about 20 minutes of processed feedstock to the gasifiers at a feed rate of about 420 tons/day in the preferred embodiment of this disclosure. A moving floor in the bin may transfer the processed feedstock to a scalping apron conveyor that meters the feedstock and may deliver it to a belt conveyor that weighs the feedstock utilizing a belt scale. Finally, the feedstock may be transferred to a distribution drag conveyor for distribution to one or more (and preferably three in the preferred embodiment of this disclosure) gasifier metering bins. Feedstock that is not discharged into one of the bins may be dropped onto a return conveyor and sent back to the front end of the distribution drag conveyor.

Each gasifier metering bin may, in the preferred embodiment of this disclosure, have a capacity of 250 cubic feet, and may be dedicated to one of the gasifier trains. The metering bins may preferably be cone-shaped with their large diameter at the bottom to avoid bridging. Each bin may preferably have a live bottom screw that discharges the feedstock to an airlock screw conveyor, where the feedstock may be compressed to form a "barrel-plug" to prevent hot gasses from back-flowing from the gasifiers into the bins. The airlock screw conveyor may preferably be tapered along the length of the screw. A lump breaker at the discharge of each airlock screw conveyor may break up the "barrel-plug" before the feedstock is transferred to the airlock discharge chute that feeds the gasifier. Each discharge chute may preferably be equipped with an airlock gate valve that closes if the back flow of hot gases is detected.

The feedstock processing building and the processed feedstock storage building may preferably be provided with dust collection, odor control and fire suppression systems. The outside conveying system that transports the feedstock to the gasifiers may also be provided with a dust collection system. Each dust collection system may preferably consist of a bag house and an induced draft fan. Plant air may preferably be used to remove dust from the bags through a bag pulsing system. Dust removed from each the bag house may be sent to the residue collection conveyer for disposal.

In one embodiment, dust may be extracted from various parts of the process. Once aggregated, the dust may then be combined or transported with the feedstock that goes into the gasification units.

Although the feedstock may vary greatly in composition, example nominal values for the composition of the material remaining after the feedstock is recycled and sorted are listed in Table 1 below.

TABLE 1

Example Ultimate Chemical Composition of Feedstock

| Feedstock Constituent | Approx. Weight (Percent) |
|---|---|
| C | 45.0 |
| H | 5.5 |
| O | 17.0 |
| N | 0.3 |
| S | 0.3 |
| Cl | 0.3 |
| Oxide | 10.0 |
| Metal | 2.0 |
| $H_2O$ | 19.6 |

The residual materials preferably excluded by the processing, storage, and handling process may include metals, rocks, dirt, concrete, PVC, and wet organic materials (wet food materials). Preferably, under normal conditions, the reject rate will run between about 10% and about 30% of the total feed rate to the material processing unit. All such materials are solids at ambient conditions. Preferably, they will be individually separated from the feedstock, deposited in a container, and transported to a landfill or composting operation, or sent for recycling or disposal off-site in accordance with applicable governmental regulations.

Gasification

In the preferred embodiment of this disclosure, the gasification unit 20 includes three gasification trains, each with about 140 tons per day processing capacity are provided to meet the total preferred plant processing capacity of about 420 tons/day. In light of this disclosure, one of skill in the art will know how to scale the facilities appropriately for different capacities.

Figure 2:
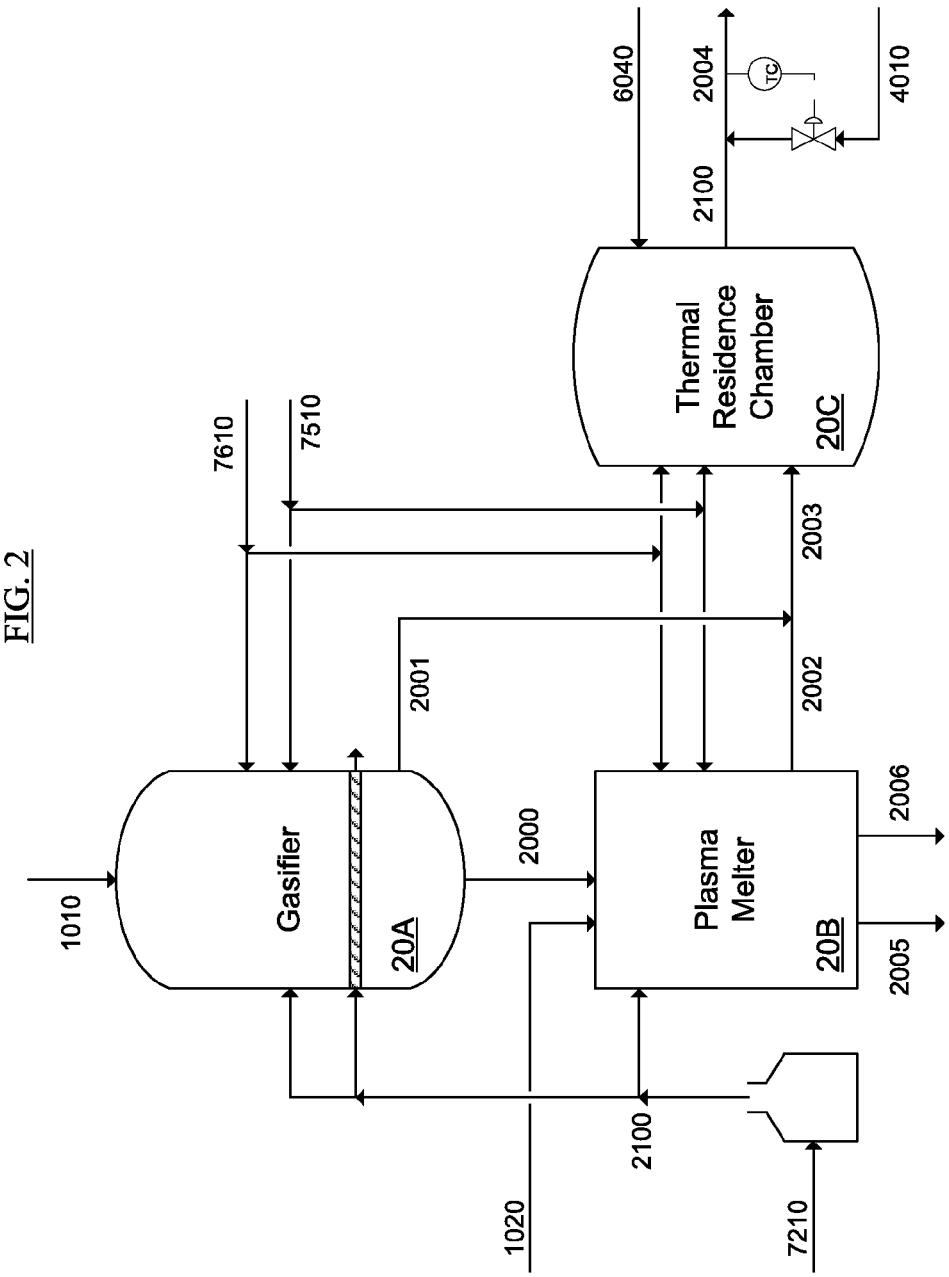
FIG. 2 shows an example of one embodiment of a gasification train for converting MSW into syngas.

FIG. 2 shows an illustrative example of one of these gasification trains. Each gasification train comprises one or more syngas generation units, and preferably includes a gasifier, a plasma melter, and a TRC. In one embodiment, a feedstock 1010 enters a gasifier 20A which produces a first syngas 2001 and a non-gasified material 2000. The non-gasified material 2000 passes in this embodiment to a plasma melter 20B into which is also fed glass cullet 1020, which produces vitrified inorganic materials and metal products (2005 and 2006, respectively) and a second syngas 2002. Syngas 2001 and syngas 2002 may in this embodiment be combined into syngas 2003 and sent to a TRC 20C, which produces a third syngas 2100. Oxygen 7510 may be fed to the gasifier 20A, plasma melter 20B, and/or TRC 20C. BFW 7210 may be boiled to steam 2100 and this steam (and/or, optionally, some other source of steam) may be fed to the gasifier and/or the plasma melter. In one embodiment, fusel oil 6040 produced downstream in the alcohol synthesis process may be fed to the TRC.

In another embodiment, syngas 2100 may be at least partially quenched by a relatively cool syngas recycle stream 4010 from downstream in the overall alcohol synthesis process, to produce a cooled mixture 2004. In a preferred embodiment, there is a mixing point having one inlet for syngas 2100, a second inlet is for syngas 4010, and an outlet for syngas 2004. In the 2004 stream, there may be a temperature sensor and a control loop which opens a valve to the 4010 stream if the temperature rises above a certain predefined level. In normal operation, syngas 2100 may continue through the mixing point and becomes syngas 2100. If the temperature sensor rises above a certain level, however, the valve to the 4010 stream may open, and the relatively cool syngas 4010 may quench the hot syngas 2100. Alternatively, and even more preferably, the valve to the 4010 stream may be continuously controlled to maintain a mixed temperature at some predefined temperature, preferably between about 649 and 760° C. (about 1200 and 1400° F.), for the combined syngas stream 2004.

Gasifier 20A preferably uses thermochemical technology in an oxygen-lean, non-combustion reducing environment. It is most preferably a down-draft partial oxidation gasifier, comprising a refractory lined vertical vessel. Preferably, the gasifier may convert at least about 80% by weight of the feedstock into syngas. In a particularly preferred embodiment, the gasifier 20A is a refractory-lined vertical vessel with a water-cooled grate in the lower section of the vessel to support a fuel bed. The gasifier preferably operates at near atmospheric pressure and at temperatures preferably between about 849° C. and about 899° C. (about 1,560° F. and about 1,650° F.). Steam 2100 and oxygen 7510 may be introduced into the gasifier to react with the feedstock to produce syngas and solid residue comprising inorganic and non-gasified organic compounds. A grate in the bottom of the gasifier may allow the non-gasified material 2000 to drop into the plasma melter 20B preferably located below the gasifier. In one embodiment, a mechanical rake may move char, ash and other solids across the grate and into the plasma melter. A small portion of the solid material ("fly ash") may remain entrained with the syngas stream 2001 and may flow into the downstream TRC 20C. A hood is preferably provided over the top of the gasifier to help provide for a safe working environment for operation and maintenance activities above the gasifier. A gasifier cooling air blower may pull ambient air under the hood and exhaust the heated air to the atmosphere at a safe location.

During start-up, the gasifier 20A may be preheated to its operating temperature before the gasification process can initiate. Therefore, the gasifier may be supplied with a down-fired gas burner designed to fire through the wall of the vessel. A gasifier burner combustion Blower supplies combustion air to the burners. The gasifier preheater system may be sized to allow the gasifier temperature to increase from ambient to operating temperature at the maximum rate allowed by the refractory lining.

In addition to the gasifier described above, other gasifiers are known in the art, including various down-draft partial oxidation gasifier designs. One may select any number of such gasifiers for use in accordance with this disclosure.

The gasifier and other syngas generation units preferably use at least about 99.5% pure oxygen, which may be prepared in an on-site cryogenic oxygen plant or other means that may be more energy efficient. Alternatively, liquid oxygen may be transported to the site, stored, and withdrawn for use from a liquid oxygen storage tank.

If the gasification unit 20 uses a plasma melter 20B, glass cullet (ground glass) may be added to maintain the proper glass level within the chambers. The glass may in one embodiment be received in supersacks and bag handling structures provided to individually feed each gasifier train. Each bag handling structure may utilize a hoist and trolley system to lift a supersack from the ground and place it on top of its dedicated discharge hopper. The supersack may manually be emptied into the hopper using a hinged access door. A slide gate at the bottom of the hopper may then be manually opened to supply the glass to a feeding system which might be dedicated to a particular plasma melter.

A plasma melter accomplishes both gasification and vitrification operations. The non-gasified material and ash 2000 leaving the gasifier may fall into the plasma melter chamber where it is exposed to a plasma-arc that provides the intense energy needed to rapidly gasify the remaining organic material. Steam and oxygen may be introduced into the plasma melter to react with the gasified organic material and produce syngas 2002. The vapor space within the chamber may preferably operate at an approximate temperature of 1,198.8° C. (approximately 2,190° F.).

Any glass-type materials entering the plasma melter chamber 20B from the gasifier 20A may be melted by the plasma-arc and fall to the bottom of the chamber to form a molten glass pool. Glass cullet and other glass-forming additives may be added separately to the plasma melter chamber in order to maintain the desired molten glass pool level in the plasma melter. Metals that were not removed in the feedstock processing section may also melted by the plasma-arc and form a separate molten layer in the bottom of the chamber under the molten glass. The mineral material in the feed that is not melted by the plasma-arc may fall into the molten glass pool to be vitrified in the glass waste product. The molten glass and molten metal may independently be withdrawn from the bottom of the plasma melter chamber and processed by separate product handling systems. The molten glass may preferably flow continuously onto a frittering vibratory conveyor that cools the glass to approximately 232° C. (approximately 450° F.) utilizing cooling water which fractures the glass into small pieces. The glass pieces then may preferably fall onto a wet conveyor that utilizes direct contact evaporative water-cooling to cool the glass to approximately 121° C. (approximately 250° F.) or less for disposal. The molten metal may be withdrawn intermittently and deposited into large refractory molds that may be cooled with ambient air to cast the metal into ingots for disposal.

In one embodiment, any remaining inert material that enters the gasifier and plasma melter, including fines, grit and smaller inorganics that are not screened out by the front-end processing system, may be expected to become encapsulated in a vitrified byproduct that is non-leachable and can be recycled into road aggregate cement products or used for landfill cover.

DC power may be used to produce the plasma-arc for the plasma melter 20B. The plasma-arc power may preferably be supplied through consumable graphite electrodes that enter the top of the vessels. The graphite electrodes may be added in segments from outside of the vessels. The use of graphite electrodes may result in a plasma-arc system with an electrical efficiency of about 98%. The DC power system may provide most of the energy required for gasification of the waste that enters the plasma melter.

An independent AC power source may heat and maintain the molten glass pool temperature through electrodes positioned below the glass surface. The maximum operating temperature of the molten glass bath is preferably about 1,648.9° C. (about 3000° F.); however, lower operating temperatures may more preferably be maintained to maximize the refractory liner life. The AC power system may also used to maintain the plasma melter close to its operating temperature during temporary shutdowns that can last from a few hours to weeks, if required. By maintaining the plasma melter near its normal operating temperature, short maintenance activities or intermittent operations may preferably be accommodated without draining all of the glass resulting in a lengthy startup procedure. This operating mode may also preferably preserve the refractory life by reducing the number of thermal transients associated with startup and shutdown activities.

A hood may be provided over the top of the plasma melter to help provide for a safe working environment for operation and maintenance activities above the plasma melter. A plasma melter cooling air blower may be provided to pull ambient air under the hood and to exhaust the heated air to the atmosphere at a safe location.

In addition to the plasma melter described above, any number of other plasma melters may be used in conjunction with the other units described in this disclosure.

The combined syngas stream 2003 from the gasifier 20A and plasma melter 20B may be routed to a TRC 20C. Additionally, a fusel oil stream 6040 from some location downstream of the gasifier unit 20 may be injected into any of the TRCs. If three TRCs are used in the process, then preferably, fusel oil may be injected into any two of the three TRCs. Injection of fusel oil stream 6040 serves to recycle the heavy alcohol compounds produced in the reactors of the alcohol synthesis unit 50, and separated in the purification unit 60, discussed below. The TRC 20C may preferably be a refractory-lined cylindrical chamber that provides additional residence time for syngas production in the presence of oxygen. The oxygen 7510 may preferably be injected into the TRC through side ports located just above the syngas 2003 inlet nozzle, for reaction with the synthesis gas to generate heat to maintain the chamber at the desired operating temperature. The reactions in the chamber may thermally crack the organic compounds present in the raw syngas 2003 and the fusel oil 6040 to allow the gasification reaction to reach or approach equilibrium.

During start-up, the TRC may preferably be preheated to operating temperature with a gas-fired burner similar to that described above for preheating the gasifiers. A TRC preheater blower may supply combustion air to the burners. The TRC preheater may be mounted near the syngas inlet nozzle and preferably be sized to heat the TRC from ambient to operating temperature at the maximum rate allowed by the refractory lining.

Waste Heat Recovery

In the preferred embodiment of this disclosure, the syngas 2100 coming from the gasification unit 20 is very hot, preferably approximately 1,348.9° C. (approximately 2,460° F.), and may include a mixture of hydrogen, carbon monoxide, carbon dioxide, methane, nitrogen, steam, acid gases, and particulates. In the preferred embodiment of this disclosure, the pressure of syngas 2100 is very roughly at or near atmospheric pressure, although this pressure is not critical, and the syngas can have a wide range of pressures. In one nonlimiting example, the pressure in 2100. Waste heat recovery unit 30 includes a mechanism for recovering some of the heat from the hot syngas effluent and using it to do work, preferably by converting it to steam and then to electrical power in a steam turbine.

Figure 3:
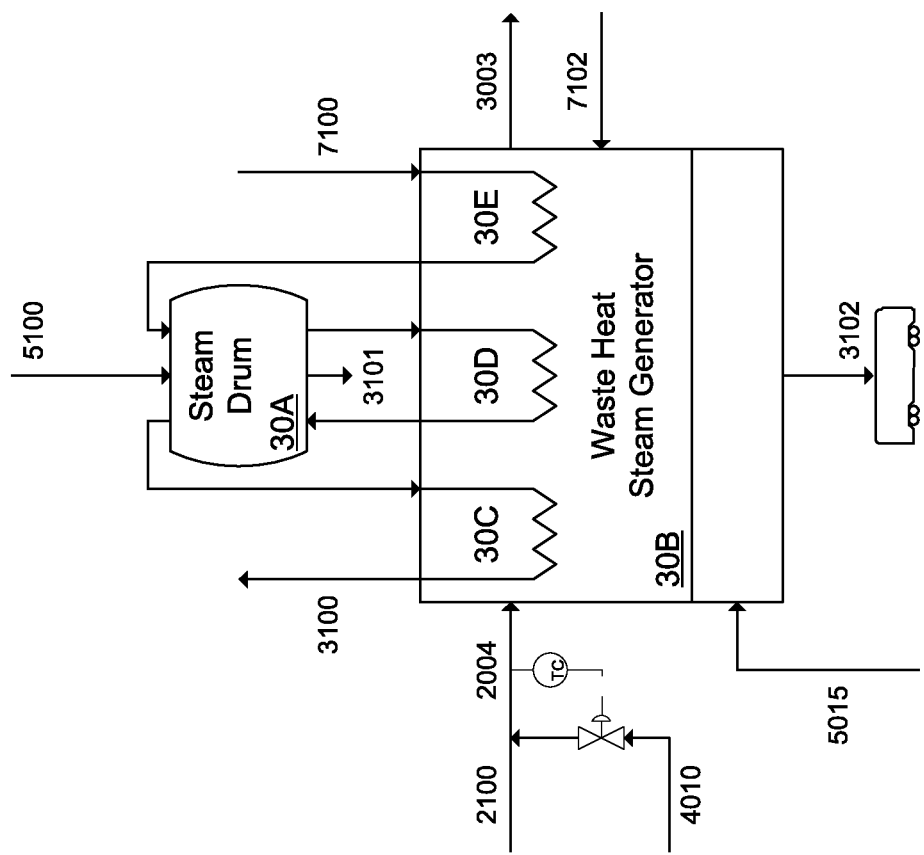
FIG. 3 shows one way to recover waste heat from a gasification effluent in accordance with the present disclosure.

FIG. 3 illustrates a preferred embodiment of a way to recover heat from the gasification effluent. The hot syngas stream 2100 from gasification unit 20 may combine with a cooled syngas quench stream 4010 that may be recycled from the discharge of the downstream syngas source at relatively low temperature, preferably from the syngas cleanup and compression unit 40. In a preferred embodiment, the amount of recycled syngas may be continuously controlled to maintain a mixed temperature at approximately 760° C. (approximately 1400° F.) for the combined stream 2004, or each combined stream 2004 if there are multiple 2100 syngas effluent streams. In the preferred embodiment, the temperature of stream 2100 will be higher than 760° C. (1400° F.), such as roughly 1371° C. to 1538° C. (roughly 2500° F. to 2800° F.), although the precise temperature at the gasification outlet will depend upon a number of factors known in the art, and may be arbitrarily increase or decrease without changing the essential nature of the process.

Waste heat recovery may take place in a waste heat steam generator (WHSG) 30B. Preferably, each hot syngas stream 2100 from the gasification unit may have its own dedicated WHSG, when there are multiple streams 2100, such as the three streams from three TRCs exemplified by the preferred embodiment of this disclosure. In some configurations, a plurality (e.g., three) of TRCs may merge their hot syngas into a single stream which may pass through a single WHSG. Each WHSG 30B may preferably recover heat from the syngas stream 2004 by preheating BFW 7100 in economizer 30E, generating saturated steam, preferably at about 800 psig in steam generator 30D, and superheating the steam in superheater section 30C, preferably along with steam 5100 that may be produced by synthesis reactors in the alcohol synthesis unit 50 and let down to match the pressure of steam drum 30A, or preferably about 55.2 bar (about 800 psig). Preferably all of the superheated steam 3100 produced in WHSG 30B may be sent to electricity generation unit 70, which may contain a steam turbine generator to produce electrical power. WHSG 30B may preferably be designed for an exit temperature of approximately 176.7° C. (approximately 350° F.) so that the syngas 3003 is cool enough to flow into a wet scrubbing section within the syngas cleanup and compression unit 40, and hot enough to stay above the dew points of any acid gas components. A skilled engineer, based on this disclosure, may optimize this temperature and adjust it appropriately. Preferably, if multiple WHSG units are used, the syngas outlets for each of them may be combined into a single syngas stream 3003.

Each WHSG may have a dedicated steam drum 30A and may preferably utilize natural circulation for the steam production. Each drum may be supplied with one or more continuous and/or intermittent blowdown facilities 3101 to maintain water quality.

Some particulate matter may fall out of the cooling syngas stream 2004 and drop into the bottom of the WHSG. Additionally, slag or ash might collect on the tubes of the WHSG. Such solids may preferably be removed by blowing steam 7102 from soot blowers and collected in the bottom of the WHSG. In one embodiment, a stream of carbon dioxide 5015 extracted from syngas downstream in the overall process may be injected into the WHSG to help remove ash. The collected ash 3102 may periodically be removed from the WHSG and conveyed to a disposal location.

In an alternative illustrative embodiment, waste heat may be recovered by using the hot syngas in one or more heat exchangers to heat oil, which may be circulated through a loop to a steam generator, which steam may them be used to generate electricity. In this embodiment, the stream of hot oil may be recirculated via a pump, and the resulting hot oil may be passed through a steam generator and hot oil cooler and stored in a hot drum before being recirculated through the loop.

Syngas Cleanup and Compression

After recovering waste heat in unit 30, the syngas may pass to syngas cleanup and compression unit 40, where it may be compressed and cleaned of undesirable contaminants such as, for example, particles, acids, mercury, and/or hydrochloric acid (HCl).

Figure 4:
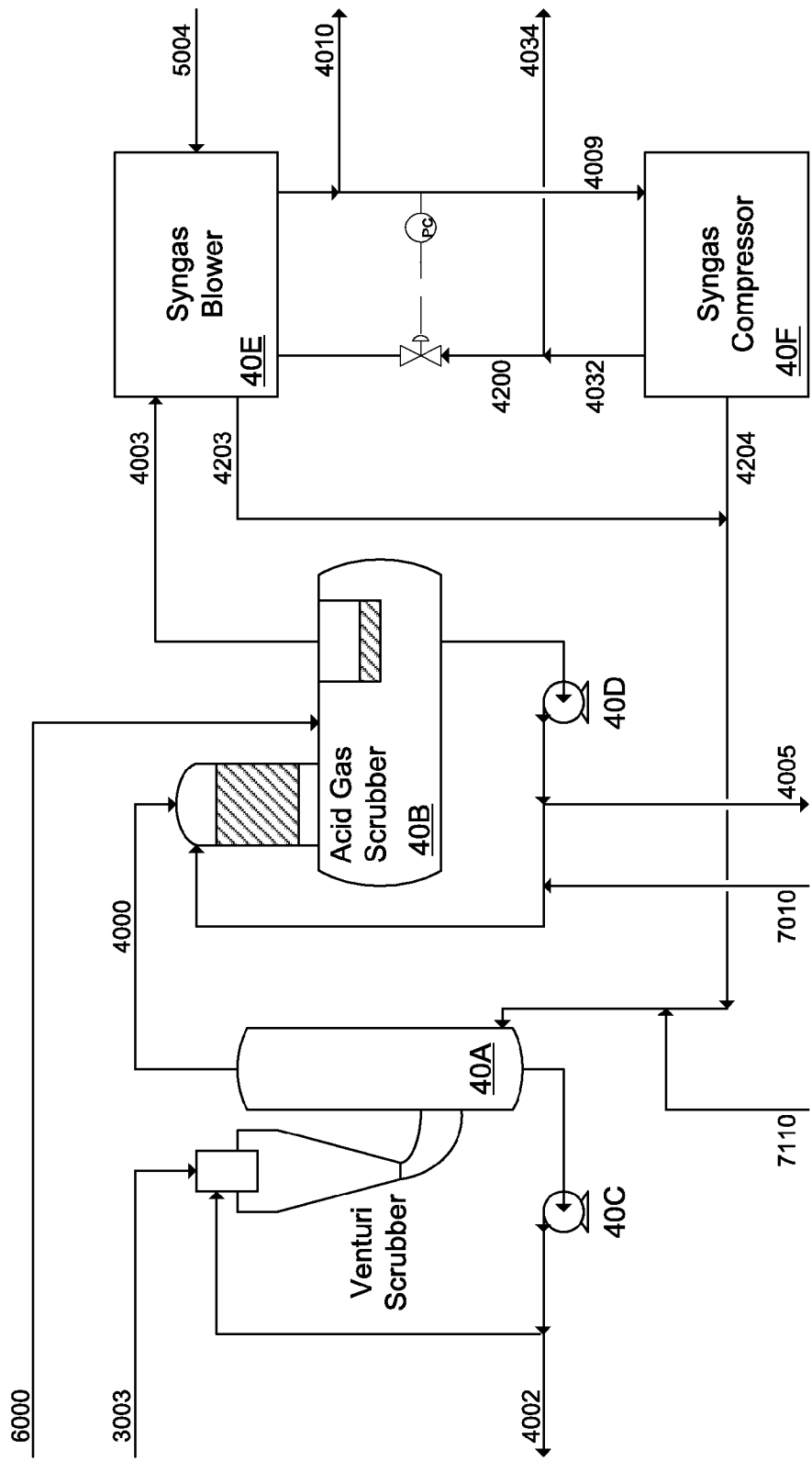
FIG. 4 shows an overview of one embodiment of a syngas cleanup and compression unit for use with the present disclosure.

FIG. 4 is an overview illustration of a possible syngas cleanup and compression unit 40. Syngas 3003 from the waste heat recovery unit 30 may contain particulate matter and chemical constituents that could impact the required metallurgy of downstream equipment and poison catalysts used for ethanol synthesis. Examples of such contaminants, which are preferably removed in the unit 40, are ash particulates, heavy metals such as mercury (Hg), lead (Pb) and chromium (Cr), and acidic compounds such as hydrogen chloride (HCl) and hydrogen sulfide ($H_2S$).

Syngas 3003 may flow into a Venturi scrubber 40A. The scrubber may utilize a circulating water stream to cool the syngas to its saturation temperature and remove preferably at least about 99.9% of the ash particulates and metals. In addition, the Venturi Scrubber may also serve as a first-stage acid gas scrubber. The circulating water solution and the syngas stream may be separated in the separator section of the scrubber. The Venturi scrubber recirculation pump 40C may take suction from the bottom of the separator section and pump the water back to the scrubbing section. A bleed stream 4002 from the discharge of the pump may be sent to a wastewater storage tank to remove solids and neutralize acidic components in the system. Reclaimed water 7110 may be added to the system in the separator section of the Venturi scrubber to maintain the liquid inventory.

The syngas 4000 from the Venturi scrubber 40A then may flow to an acid gas scrubber 40D, which may in one preferred embodiment comprise a static mixer section on top of a knockout drum. Circulating caustic or other alkaline solution such as hydrated lime may combine with syngas stream 4000 and the mixture may flow down through the static mixer to remove acidic compounds from the syngas. The preferably brief contact time between the syngas and the alkaline solution in the static mixer may achieve an HCl content of less than about 1 ppm in the treated syngas stream 4003 while minimizing the consumption of the alkaline solution resulting from the undesirable removal of carbon dioxide ($CO_2$). The treated syngas 4003 may exit the top of the knockout drum and flow to a system of one or more syngas blowers within a syngas blower unit 40E. An alkaline solution circulation pump 40D may be utilized to circulate the alkaline solution from the bottom of the drum back to the inlet of the static mixer. Fresh alkaline agent 7010 may be added to the circulating solution to maintain a predefined pH range, and partially spent solution 4005 may be purged from the system to maintain a constant level in the knockout drum. The alkaline solution purge stream 4005 may be sent to a wastewater storage tank, where it may preferably assists in the neutralization of the acidic blowdown stream 4002 from the Venturi scrubber.

The supply of alkaline solution may preferably comprise a concentrated solution of approximately 50 wt % caustic which is kept in storage in a tank, or lime which may be in hydrated or anhydrous form. To dilute the alkaline solution to the desired concentration, a specified amount of TRIGID water may be added to the tank. A pump may then be used to circulate the solution through a cooling device, preferably a heat exchanger using cooling water, and a jet mixer located inside the tank to homogenize the diluted solution and remove heat generated by the dilution process. After mixing is complete, the supply of fresh alkaline solution to the syngas cleanup and compression unit 40 may be resumed using a caustic supply pump.

Syngas 4003 from the acid gas scrubber 40B may flow to a syngas blower unit 40E, an example of which is described below. The syngas outlet of blower 40E may be split into net syngas stream 4009 which may pass to a syngas compressor 40F, and one or more syngas quench streams 4010, which may be used as described above to quench the hot gasifier syngas effluent.

Syngas 4009 may be compressed to high pressure in a syngas compressor system 40F. In one illustrative embodiment of a suitable syngas compressor, the net syngas stream 4009 may be compressed from approximately 15 psig for syngas 4009 to approximately 100 bar (approximately 1450 psig) for syngas 4032. In another higher-pressure embodiment, the pressure of syngas 4032 may be in the range of about 103.4 to 151.7 bar (about 1500 to about 2200 psig). The pressure in stream 4032 may be roughly about the same pressure as the reactor(s) in the alcohol synthesis unit 50. In one embodiment, the pressure in the reactor(s) may be controlled by manipulating the power of the syngas compressor 40F through any control means known in the art. Part of the high pressure syngas 4032 leaving the syngas compressor 40F may preferably be drawn off as a compressor spillback stream 4200, which may recycle to the syngas blower 40E, preferably to control the pressure of the syngas inlet 4009.

The suction pressure of syngas 4009 at the inlet of the syngas compressor, which is preferably essentially the same as the discharge pressure of the syngas blower, may in one embodiment be maintained at approximately 1 bar (approximately 15 psig) by spillback control from the outlet of the syngas compressor to the outlet of the syngas blower. In this preferred embodiment, maintaining 1 bar (15 psig) at the discharge of the syngas blower may provide sufficient pressure to send cooled quench gas 4010 to the inlet of the waste heat recovery unit 30.

Syngas outlet 4034, representing whatever of syngas 4032 that is not recycled to the outlet of the syngas blower, is the outlet of the syngas cleanup and compression unit 40, which may flow to the alcohol synthesis unit 50.

Figure 5:
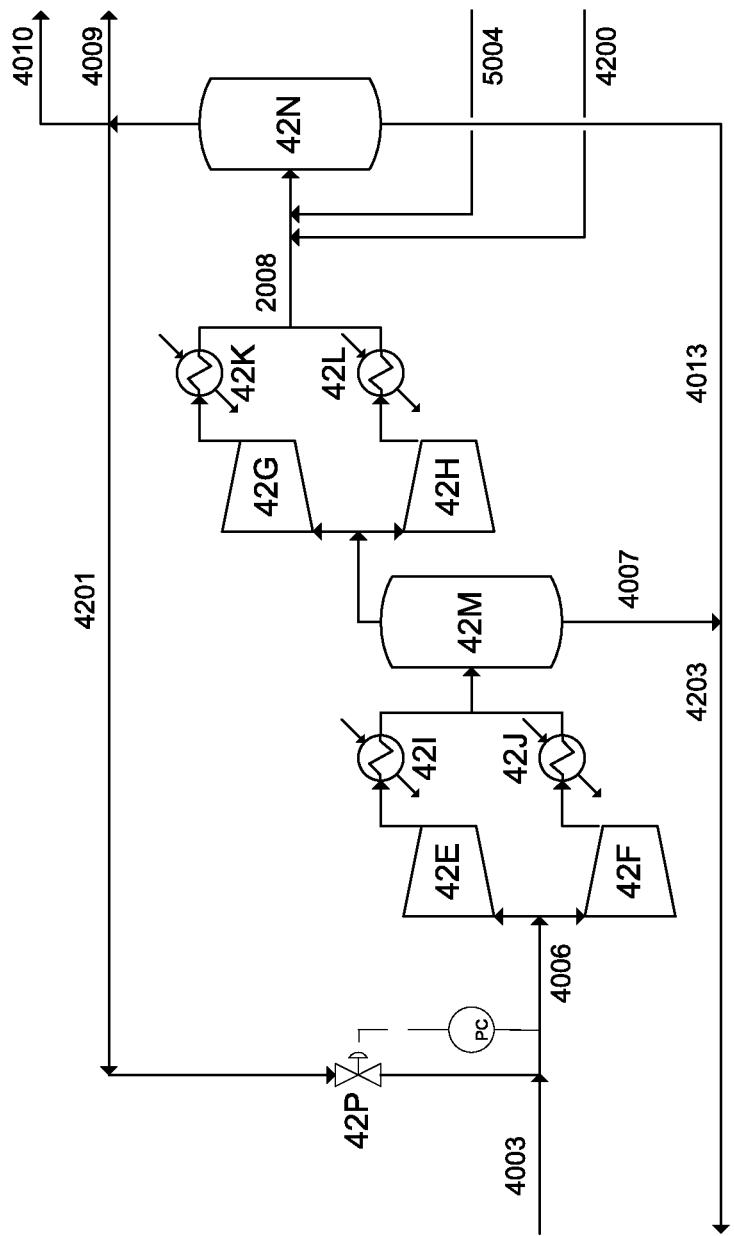
FIG. 5 shows an illustrative example of a syngas blower for use with the present disclosure.

FIG. 5 is an illustrative example of a syngas blower 40E. Syngas 4003 from the acid gas scrubber 40B may preferably flow directly to the suction of the first of one or more parallel syngas blowers, which may contain multiple stages. In one embodiment, two rotary-type compressors 42E and 42F may operate in parallel, with each preferably sized for about 50% of the design flow rate. The discharge from each machine may flow through syngas blower interstage coolers 42I and 42J utilizing cooling water. The cooled parallel streams may combine and flow to a common syngas blower interstage knock-out drum 42M. Any condensed liquid 4007 from the intercoolers may be separated from the gas stream in knock-out drum 42M and recycled back to the Venturi scrubber 40A. The syngas stream from knock-out drum 42M may split and flow to the suction of a second set of compression stages of syngas blowers. Similar to the first stage, two rotary-type compressors 42G and 42H may operate in parallel with each preferably sized for approximately 50% of the design flow rate. The discharge from each machine may flow through syngas blower after coolers 42K and 42L that utilize cooling water. The cooled parallel streams may combine (4008) and flow to a common syngas blower knock-out drum 42N. This drum may also preferably receive a compressor spillback stream 4200 from a syngas compressor 40F, and/or a flash gas stream 5004 from a location downstream in the overall process, preferably in the alcohol synthesis unit 50. Any condensed liquid 4013 from the after coolers may be separated from the gas stream in knock out drum 42N. Liquid 4013 may form a part of any condensed liquid 4007 from any knock-out drums within the syngas blower system 40E, and all such liquid 4203 may preferably be recycled back to Venturi scrubber 40A. In one embodiment, compressors 42E, 42F, 42G, and 42H may be internally-geared centrifugal compressors.

At the outlet of syngas blower knock-out drum 42N, the compressed stream may be spilt into the net syngas stream 4009, a compressor spillback stream 4201 and one or more syngas quench streams 4010, which may be used as described above to quench the hot gasifier syngas effluent. The net syngas gas stream 4009 may flow directly to syngas compressor 40F. The compressor spillback stream 4201 may be sent back to the suction of the first stage (e.g., 42E and/or 42F) of the syngas blower. The flow rate through a spillback control valve 42P may preferably be automatically controlled to maintain an operating pressure of at least atmospheric pressure, or preferably approximately 1 psig, as syngas 4006 enters the first stage of syngas blowers (e.g., 42E and/or 42F). This control point may help ensure that the lowest operating pressure in the system is maintained slightly above atmospheric pressure and does not drop to a vacuum condition.

Figure 6:
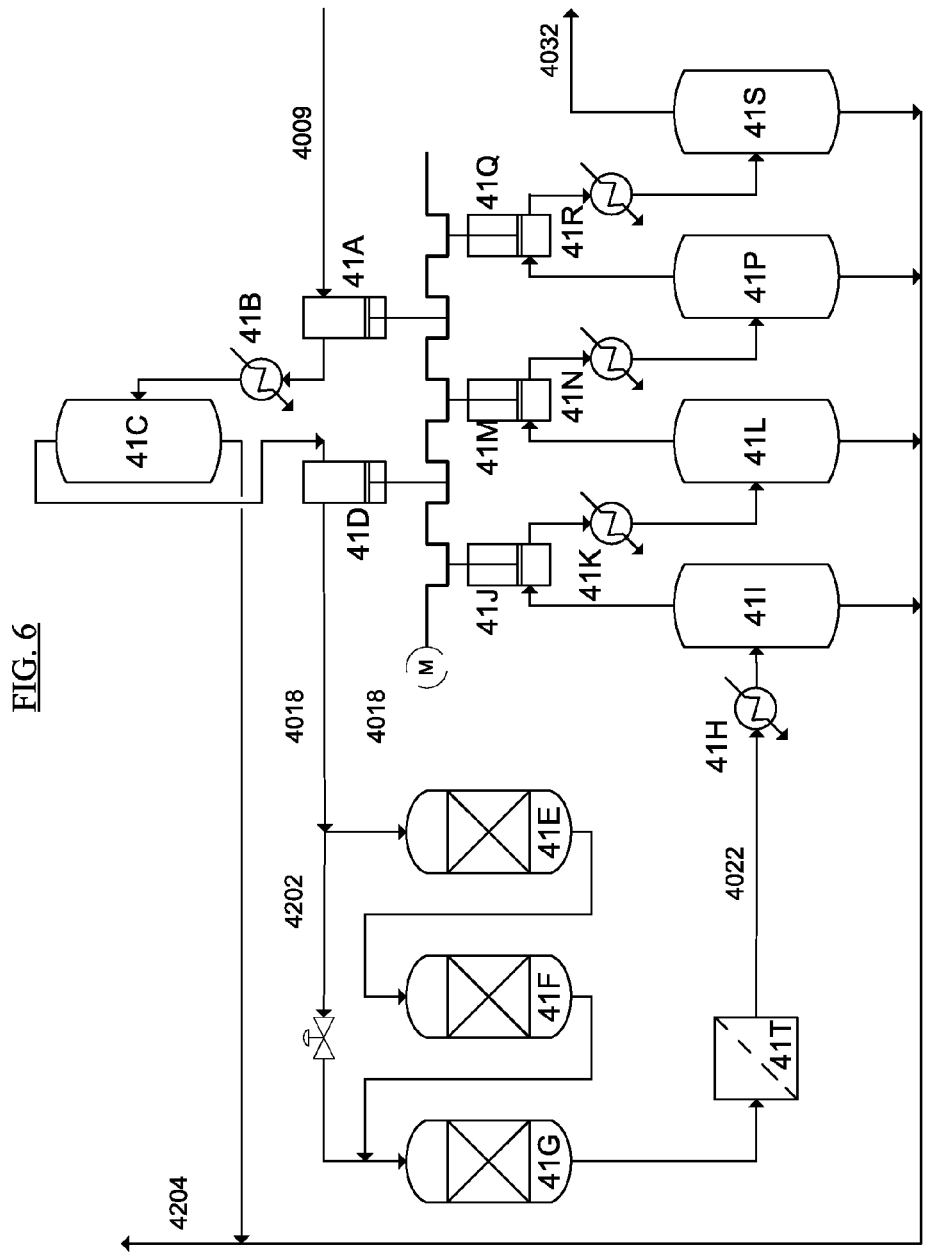
FIG. 6 shows one illustrative example of a syngas compressor for use with the present disclosure.

FIG. 6 is one illustrative example of a syngas compressor 40F. The net syngas stream 4009 may be compressed from approximately 1 bar to approximately 100 bar (approximately 15 psig to approximately 1450 psig) by 5 reciprocating stages of compression in a syngas compressor. The precise pressure to which the stream is raised will be dictated primarily by the desired equilibrium conditions for the reactors in the alcohol synthesis unit 50. The syngas may flow to the first stage 41A of the syngas compressor where it may be compressed to approximately 3.4 bar (approximately 50 psig) and then cooled in the syngas first stage intercooler 41B preferably utilizing cooling water. Any liquid 4204 that condenses in the intercooler may be knocked out in the syngas compressor first stage knock-out drum 41C and preferably recycled back to Venturi scrubber 40A. The syngas then may flow to a second stage 41D of the syngas compressor where it may be compressed to approximately 8.9 bar (approximately 130 psig). After the second stage of compression, the hot syngas may preferably be sent to a series of guard beds (e.g., 41E, 41F, and/or 41G) to remove traces of mercury, chlorine, and other catalyst poisons that may be present in the gas stream. The treated syngas may then return to the compression section and be cooled in a syngas compressor second state intercooler 41H preferably utilizing cooling water. Any liquid 4204 that condenses in the intercooler may be knocked out in a syngas compressor second stage knock-out drum 41I and recycled back the Venturi scrubber 41A.

The syngas then may flow to a third stage 41J of the syngas compressor where it may be compressed to approximately 20.7 bar (approximately 300 psig). After compression the gas may be cooled in a syngas compressor third stage intercooler 41K preferably utilizing cooling water. Any liquid 4204 that condenses in the intercooler may be knocked out in a syngas compressor third stage knock-out drum 41L and preferably recycled back the Venturi scrubber 40A. The syngas may then flow to a fourth stage 41M of the syngas compressor where it may be compressed to approximately 44.5 bar (approximately 645 psig). After compression the gas may be cooled in a syngas compressor fourth stage intercooler 41N, preferably utilizing cooling water. Any liquid 4204 that condenses in the intercooler may be knocked out in the syngas compressor fourth stage knock-out drum 41P and preferably recycled back to Venturi scrubber 40A. Finally, the syngas may flow to a fifth stage 41Q of the syngas compressor where it may be compressed to approximately 98.9 bar (approximately 1435 psig) and then cooled in a syngas compressor fifth stage aftercooler 41R, preferably utilizing cooling water. Any liquid 4204 that condenses in the aftercooler may be knocked out in a syngas Compressor fifth stage knock-out drum 41S and preferably recycled back to Venturi scrubber 40A. The outlet 4032 to drum 41S in this example will be compressed syngas.

At some point in the syngas cleanup and compression unit 40, preferably during an intermediate stage of compression within the syngas compressor unit 40F, the main syngas stream may be passed through a system for removing potential catalyst poisons. In one embodiment, syngas stream 4018 from syngas compressor second stage 41D may flow through one or more catalyst poison separation units prior to the final stages of compression. In a preferred embodiment, syngas 4018 flows through three guard beds. The first vessel 41E may be a mercury guard bed designed to remove mercury and other volatile metals. The second vessel 41F may be the chlorine guard bed, designed to remove HCl, acid gas components, and other potential catalyst poisons. The final vessel 41G may be a combined guard bed designed to remove catalyst poisons that have broken through the first two beds. During normal operation, the syngas may flow through all three guard beds in series. If a breakthrough is detected at the outlet of either of the two primary guard beds, both primary guard beds 41E and 41F may be temporarily bypassed to allow for adsorbent replacement, with the combined guard bed 41G remaining online to protect the downstream synthesis catalyst. The combined guard bed 41G may also be temporarily bypassed (4202) to allow periodic replacement of adsorbent to ensure that it is always available to protect the downstream catalyst. The two primary guard beds 41E and 41F may preferably be sized to provide an estimated adsorbent life of about 1 year, while the combined guard bed 41G may preferably be designed to last several years, given that it normally operates downstream of the primary beds. Before returning to the syngas compression section, the syngas may flow through a syngas guard bed filter 41T to remove any catalyst fines from the gas stream.

Alcohol Synthesis

After passing through a syngas cleanup and compression unit 40, the cleaned and compressed syngas 4034 may pass to an alcohol synthesis unit 50, where alcohol may be generated, preferably through a catalytic reactor.

Figure 7:
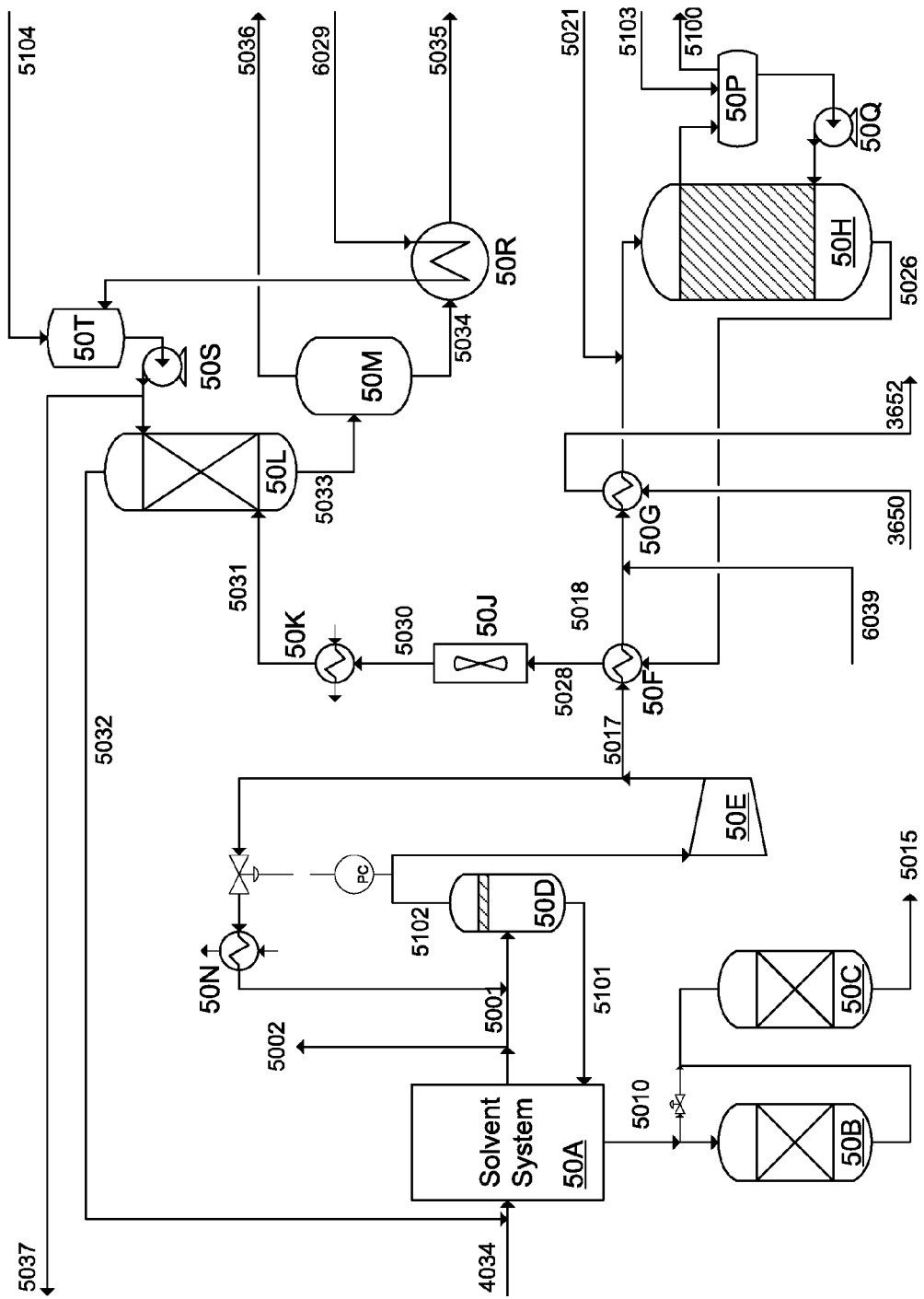
FIG. 7 shows an illustrative example of an alcohol synthesis unit for use with the present disclosure.

FIG. 7 shows an illustrative example of an alcohol synthesis unit 50. Compressed syngas 4034 from the syngas cleanup and compression unit 40 may preferably be combined with a recycle gas stream 5032 containing unreacted syngas from a reactor effluent stream, and fed to a solvent system 50A, in which carbon dioxide may be removed from the compressed syngas and recycle syngas streams. Reject gas containing $CO_2$ and $H_{2S}$ may be fed to one or more sulfur guard beds 50B and/or 50C, as will be discussed In the preferred embodiment of this disclosure, the solvent system is intended primarily to remove carbon dioxide, while sulfur removal is incidental to $CO_2$ removal. In alternative embodiments, where the catalyst in reactor 50H does not require a significant amount of sulfur, removal of sulfur within the recycle stream may be more important.

Outlet sour gas stream 5010 may primarily comprise $CO_2$, and may also be expected to comprise at least a small amount of $H_2S$. In a preferred embodiment, stream 5010 may be sent to sulfur guard beds 50B and 50C to remove the $H_2S$ from the stream. The two guard beds preferably may be piped in a lead/lag configuration to allow for on-line replacement of spent adsorbent. The treated $CO_2$ reject gas 5015 from the guard beds may be utilized in the ash removal systems for the waste heat recovery unit 30, as discussed above, or vented to the flare header on pressure control.

Some of the gas 5002 which may include syngas as well as methane, ethane, and other hydrocarbons, may be purged from the recycle loop stream after leaving the solvent system 50A, to be sent to the electricity generation unit 70 which may preferably contain a combustion turbine for generating electricity. In other embodiments, the gas stream 5002 may be fed to a boiler that may be used to generate steam that which would subsequently be used to generate electricity. The remaining recycle loop syngas 5001 may flow to a recycle compressor suction drum 50D. Any liquid 5101 that may collect in the bottom of the drum may be expected to potentially contain solvent, and may therefore be sent to the solvent system to recover the solvent. The syngas 5102 then may flow to one or more recycle compressors 50E. Preferably, the recycle compressor(s) 50E may boost the operating pressure from about 98.6 bar to about 105.8 bar (about 1430 psig to about 1535 psig). In a preferable embodiment, two 100% reciprocating machines (operating in parallel) may be provided to ensure the reliability of the syngas recycle service. The suction pressure may be maintained at approximately 98.6 bar (approximately 1430 psig) by spillback control through a recycle compressor spillback cooler 50N that preferably utilizes cooling water.

From recycle compressor(s) 50E, the combined recycle gas stream and fresh feed syngas 5017 may flow to an ethanol synthesis feed/effluent exchanger 50F, where it may be heated by hot reactor effluent 5026 from one or more ethanol synthesis reactor(s) 50H. The syngas may then be combined with recycled methanol 6039 from purification unit 60, and the combined stream may be heated in a reactor feed heater 50G to the desired reactor inlet temperature (which may, in one embodiment, be about 315.5° C. or 600° F.) by heat exchange with superheated steam 3650. The heated syngas 5020 then may flow to preferably tubular-type ethanol synthesis reactor (s) 50H, described below, which convert syngas into ethanol, other alcohols, water, and possibly other related byproducts. While the specific illustrated embodiments and foregoing description herein focus on creating ethanol from syngas, those of skill in the art will recognize that other alcohols may be produced if desired by modifying the teachings of this disclosure to isolate another alcohol product from the reactor effluent stream.

In one embodiment, a small amount of sulfiding agent (preferably dimethyl disulfide) 5021 may be added to the syngas upstream of the reactors to achieve a sulfiding agent concentration of some predefined concentration that might be needed in any particular embodiment to maintain catalyst activity. The concentration of the sulfiding agent may in one embodiment be between about 20 to about 150 ppm, and preferably in the range of about 50 to about 75 ppm, on a molar basis. The addition of a sulfidization agent within the preferred range may have the benefits of reducing cracking of methanol to methane and carbon dioxide, and increased methanol and ethanol formation.

The sulfiding agent may, for example, be stored in a tote tank and injected into the syngas using a sulfiding agent injection pump. The concentration of the sulfiding agent within the syngas may be controlled in any way known in the art; for example, the concentration may be measured by a total sulfur analyzer, and then the rate of injection into the stream may be varied according to a feedback control loop. Various sulfur analyzers, including total sulfur analyzers, are known in the art. The sulfiding agent may be injected by any means known in the art, including pumps, syringes, pistons, gravity feed, etc.

Most of the reactions that may occur in the reactor(s) 50H are exothermic. The heat of reaction may be removed from the reactors by circulating boiler feed water around the reactor tubes and using the heat of reaction to produce steam 5100. One or more steam drums 50P may separate the steam from the circulating water, and in one embodiment may be shared by all of the reactors. One or more steam drum circulation pumps 50Q may be provided for the circulating water service. In one embodiment, each pump may be designed for 50% of the total design circulation rate and two pumps may operate continuously (the third pump may be used as a spare). Operating two 50% pumps may ensure that the loss of a single operating pump does not result in the loss of water circulation to the reactors. The operating pressure in the steam drum may be automatically adjusted so that the corresponding steam generation temperature provides the proper heat transfer rate required to maintain the desired reactor outlet temperatures, which in a preferred embodiment may be about 350° C. (about 662° F.). In one embodiment, the pressure in the steam drum 50P may vary between approximately 82.7 and 124.1 bar (approximately 1200 and 1800 psig) depending upon the operating conditions. The high pressure steam 5100 (preferably all of it) leaving the reactor steam drum 50P may be let down to approximately 55.2 bar (approximately 800 psig) and sent to the waste heat recovery unit 30, where it may in one embodiment be superheated by absorbing heat from the gasifier effluent.

Boiler feed water 5103 that has preferably been preheated in another part of the overall process may be added to steam drum 50P to maintain its operating level. A continuous blowdown stream may be taken from the steam drum and intermittent blowdown streams may be taken from the steam drum 50P and the reactors 50H to maintain the water quality. The continuous and intermittent blowdown streams may be routed to blowdown drums.

The reactor effluent streams 5026 from one or more reactor trains may be combined and flow through an ethanol synthesis feed/effluent Exchanger 50F to partially cool the effluent stream. The reactor effluent 5028 then may flow through an absorber feed cooler 50J where it may be cooled by ambient air, and then through an absorber feed trim cooler 50K where it may be cooled by cooling water before entering a mixed alcohol absorber 50L. The alcohol absorber 50L may preferably be a frayed column that may utilize a primarily recycled water stream to absorb the alcohol compounds from the reactor effluent stream 5031. The remaining gas stream 5032 exiting the top of the alcohol absorber may become becomes the recycle gas stream that may be sent back to the upstream process where may be combined with the fresh feed syngas stream 4034 at the inlet to the Solvent System 50A.

An absorber water feed drum 50T may receive recycle water 6029 from the purification unit 60 that may have been cooled in the tube side of an absorber bottoms/water exchanger 50R. However, a portion of the recycle water may be purged to maintain the quality of the recycle water. The absorber water feed drum 50T may also receive fresh demineralized water 5104 to maintain the level in the drum. An absorber water feed pump 50S may take suction from the drum 50T and transfer the water to the top of mixed alcohol absorber 50L. Absorber water feed drum 50T may also provide a small water slipstream 5037 from the discharge of the absorber water feed pump 50S, which may be used for degassing the mixed alcohols in the purification unit 60, as discussed below.

The mixed alcohol stream 5033 from the bottom of the absorber may be sent to an absorber flash drum 50M where preferably the majority of the gasses absorbed in the liquid stream may be flashed off. The flashed gas 5036 may be routed directly to purification unit 60, while the mixed alcohol liquid 5034 may be preheated in the shell side of the absorber bottoms/water exchanger 50R before being routed (5035) to purification unit 60. The flash drum 50M may provide a safety break between the high-pressure syngas section and the low-pressure alcohol purification section. The pressure drop may be effected by any means known in the art, including providing resistance to flow through friction, such as via a throttling valve, or by extracting work energy from a stream from the high-pressure section. One might expect a large volume of vapor to be associated with a vapor-breakthrough relief case from mixed alcohol absorber 50L. This volume may be handled by a relief valve located on the flash drum. This may avoid the need to evaluate any potential damage to the internals of relatively small diameters of components in the purification unit 60, due to any high vapor/liquid mixture velocities and also may avoid the potential for a two-phase vapor/liquid relief.

In the embodiments described above, the alcohol synthesis unit 10 may in a preferred embodiment comprise a high-pressure main syngas recycle loop, in which the entire syngas recycle loop is at a relatively high pressure compared to the pressure of the rest of the overall process, the step-up in pressure taking place at the syngas compressor 40F. In this embodiment, the main recycle loop comprises stream 4034, solvent system 50A, syngas recycle compressor 50E, alcohol synthesis reactor(s) 50H, separator 50L, and stream 5032 which is recycled to mix with stream 4034. Syngas recycle compressor 50E may be designed primarily to overcome pressure losses in the loop and keep the main syngas recycle loop circulating.

In an another embodiment, the main syngas recycle loop may be at an intermediate pressure, except for a segment of the loop comprising the synthesis reactor 50H that operates at a relatively high pressure. Upstream of reactor 50H there may be a high-pressure compressor, and downstream of the reactor there may be a turbo-expander to reduce the pressure down to the intermediate pressure of the remainder of the loop. In one embodiment, the turbo-expander may drive the high-pressure compressor from the energy derived from reducing the pressure of the hot effluent stream to match the intermediate-pressure system. This embodiment may include catalyst poison removal separator(s) (e.g., 41G, 41F, and 41E of FIG. 6) within the intermediate-pressure portion of the main syngas recycle loop, as preferably these units operate at an intermediate pressure. The intermediate pressure may be between about 8.6 bar and about 103.4 bar (about 125 psig and about 1500 psig), preferably between about 27.6-68.9 bar (about 400-1000 psig), and most preferably about 37.9-51.7 bar (about 550-750 psig).

Figure 8:
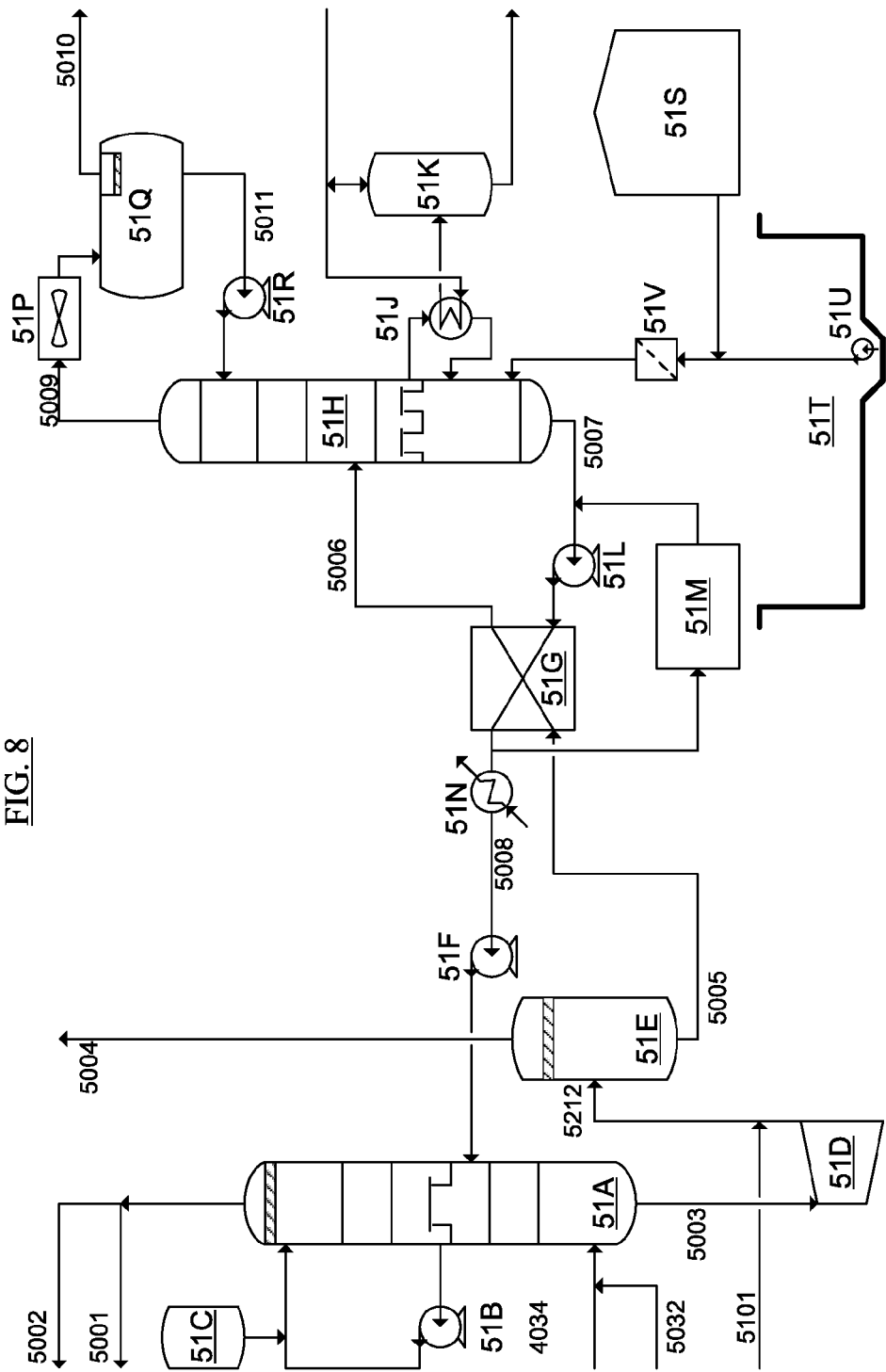
FIG. 8 shows an illustrative example of a solvent system for use with the present disclosure.

FIG. 8 shows an illustrative example of a solvent system 50A. Compressed fresh feed syngas 4034 from the syngas cleanup and compression unit 40 may preferably be combined with the recycle gas stream 5032 and sent to a solvent absorber 51A. The combined gas stream preferably enters the bottom of the absorber and flows up through the bottom trayed section of the column where it may be contacted with the solvent solution flowing down through the bottom section to remove $CO_2$ from the gas stream. The syngas then may flow up through a chimney tray into the top tray section of the column where the gas is contacted with a circulating wash water stream flowing down through the top section to recover solvent entrained in the syngas. An absorber water wash pump 51B may circulate the wash water from the chimney tray to the top of the column. A surge volume of demineralized water may be stored in a water make-up drum 51C and then pumped to the chimney tray with a water make-up pump to provide fresh makeup water. A purge stream may branch off the suction line of the water circulation pump 51B to maintain the liquid level in on the chimney tray. The purge stream may be sent to a rich solvent flash drum 51E.

The solvent absorber 51A is preferably designed with the flexibility to control the $CO_2$ content in the treated gas between approximately 1 and 5 mol % while minimizing the loss of carbon monoxide (CO) and hydrogen ($H_2$) in the syngas stream. In one illustrative embodiment, approximately 15% of the treated syngas exiting the top of the absorber flows (5002) to the electricity generation unit 70 and to a gas turbine generator therein, and the remainder flows to the recycle compressor 50E.

The rich solvent solution 5003 from the bottom of the solvent absorber MA may be sent to a rich solvent hydraulic turbine MD to recover energy from the high-pressure liquid and provide power to one or more lean solvent pumps 51F. The low-pressure rich solvent from turbine MD may combine with the water wash purge (discussed above), and may also combine with condensate stream 5101 from the syngas recycle compressor (FIG. 7, 50D, discussed above), and the combined stream 5212 may flow to the rich solvent flash drum ME. In this flash drum, preferably the majority of the $CO_2$ and $H_2S$ absorbed in the combined rich solvent/wash water stream flashes off (5004). The slightly diluted rich solvent solution 5005 then may flow through a lean/rich solvent exchanger MG to preheat the rich solvent before it enters the Solvent Regenerator 51H. The $CO_2/H_2S$ gas stream 5004 from flash drum ME may be sent to the syngas blower 40E utilizing pressure control to maintain sufficient pressure in the outlet to the syngas blower to allow the rich solvent solution to flow into the solvent regenerator 51H without being pumped.

The rich solvent solution may comprise an amine, and preferably comprises monoethanol amine. In another embodiment, the solvent comprises dimethyl ethers of polyethylene glycol. Other solvent systems capable of removing $CO_2$ and $H_2S$ are known in the art.

Steam may be condensed on the tube side of a solvent regenerator reboiler 51J to provide heat for stripping at least most of the remaining acid gases from the rich solvent solution. The steam condensate may be collected in an amine regenerator reboiler steam condensate drum 51K and then sent to a condensate flash tank.

Lean solvent 5007 from the bottom of regenerator 51H may be pumped through the lean/rich solvent exchanger 51J using a lean solvent booster pump 51L. A portion of the partially-cooled lean solvent stream may be recycled to the suction of the pump after flowing through a solvent filter package 51M to remove particulates that tend to build up in the circulating solution. The lean solvent then may flow through the lean solvent cooler 51N for additional cooling utilizing cooling water before it is pumped with lean solvent pump 51F back to the top tray in the solvent section of solvent absorber 51A. As mentioned above, at least one of the lean solvent pumps may in one embodiment be connected to the solvent hydraulic turbine 51D to recover energy from the high-pressure rich solution from the absorber and supplement its motor driver.

Overhead vapor 5009 from the regenerator may be partially condensed in a solvent regenerator overhead condenser 51P preferably by heat exchange with ambient air, and the vapor/liquid stream may enter a solvent regenerator overhead knock-out drum 51Q. The majority of the condensed liquid 5011 may be returned to the top of the solvent regenerator 51H with a solvent regenerator reflux pump 51R. However, a small water blowdown stream may be taken from the discharge of the reflux pump 51R to maintain the water balance in the solvent circulation system, which may preferably be sent to a water reclamation unit. Sour gas 5010 (which may be primarily $CO_2$ with a small amount of $H_2S$) may exit drum 51Q on pressure control, and may in one embodiment be sent to sulfur guard (e.g., 50B and 50C of FIG. 7) to remove $H_2S$ from the stream.

Fresh solvent may be brought into the plant by tank trucks or other means of conveyance and transferred to the solvent storage tank 51S. A solvent make-up pump may be used to pump make-up solvent from storage 51S, through a solvent make-up filter, and into the liquid surge section of the solvent regenerator 51H as needed. Additionally, an anti-foam package may be utilized to inject an anti-foam agent into the circulating wash water stream at the top of solvent absorber MA and the reflux stream at the top of solvent regenerator 51H.

All solvent solution drained from equipment and piping in the solvent treating area may be collected in a drain solvent sump drum 51T. The drum may be vented to a flare header and may have a continuous nitrogen purge. A drain solvent sump drum pump 51U may be utilized to intermittently pump the recovered solvent through the solvent make-up filter MV and into the liquid surge section of the solvent regenerator 51H.

Purification

Figure 9:
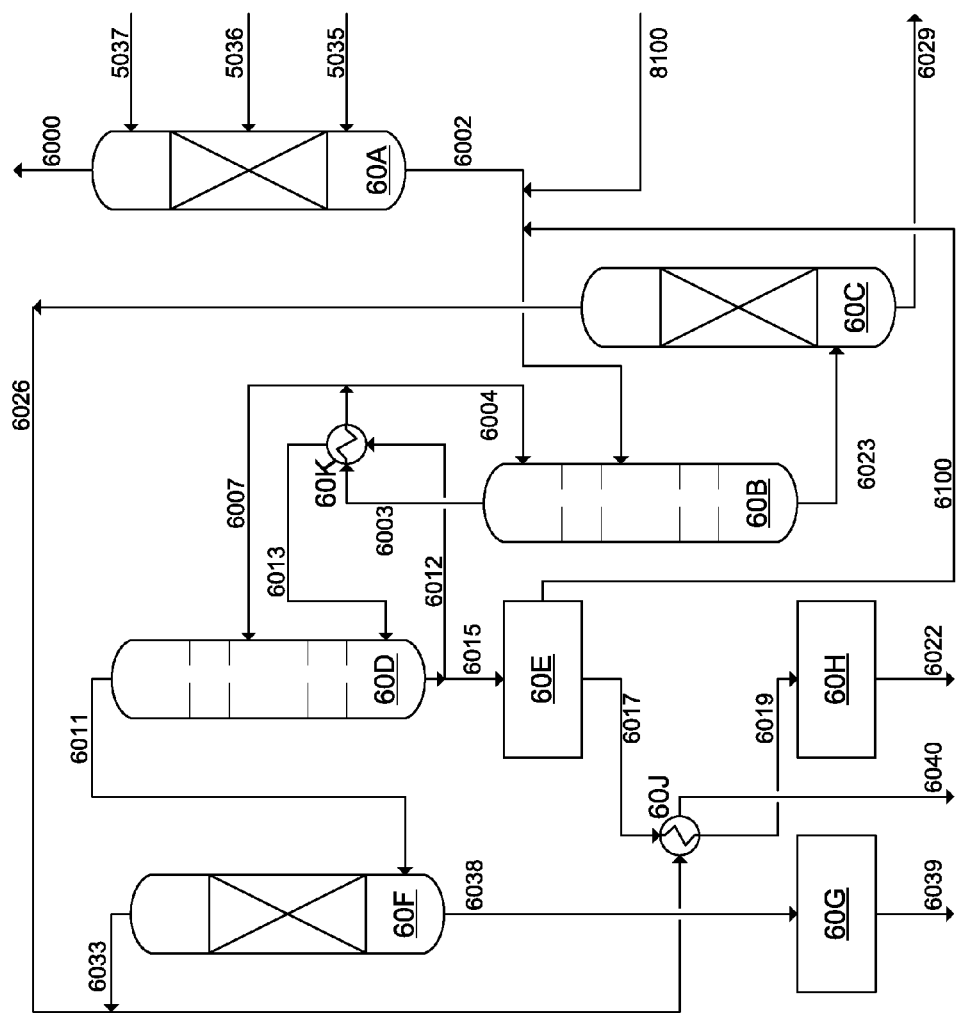
FIG. 9 shows one possible embodiment of a purification system for use with the present disclosure.

Mixed alcohols from alcohol synthesis unit 50 may be purified to separate ethanol in purification unit 60. FIG. 9 illustrates one possible embodiment of a purification system 60. Mixed alcohol liquid stream 5035, and flash gas 5036 may be sent to mixed alcohol degasser 60A. Water 5037 may be used as a reflux stream to strip the majority of the alcohol compounds that are present in the vapor. The overhead vent gas 6000 may be recycled to the syngas cleanup and compression unit 40. The mixed alcohols from the bottoms of the degasser 60A may be combined with off-specification ethanol 8100 recycled from downstream in the process, and may be sent to the methanol-ethanol/heavies separator 60B. This separator may be designed to separate methanol and ethanol in the overhead or distillate, and propanol, heavier alcohols, and water in the bottoms. A resulting propanol and heavier stream 6023 may be separated into heavy alcohol 6026 and water 6029 components in a propanol/water separator 60C. The heavy alcohol stream 6026 may preferably be vaporized in a fusel oil vaporizer 60J and fed to the gasification unit 20, and in one embodiment to a TRC within the gasification unit, where it may be partially oxidized to form carbon monoxide, hydrogen, carbon dioxide, and water. Water stream 6029 may be sent to the alcohol synthesis unit 50. for heat exchange and use in absorbing mixed alcohols from the ethanol reactor effluent, as discussed above.

In one embodiment, the vapor product 6003 of column 60B may be condensed in the overhead, for example via heat exchanger 60K, returning part of the condensed liquid 6004, and sending another part of the condensed liquid as stream 6007 to methanol/ethanol separator 60D. In this embodiment, the heat released by overhead condensation may be used to reboil column 60D.

Overhead product 6007 from column 60B may be passed to methanol/ethanol separator 60D to separate ethanol from lighter components. The overhead or distillate 6011 may contain methanol and methyl acetate. Liquid product 6012 from column 60D may in one embodiment be reboiled, for example in exchanger 60K, by utilizing heat of condensation for the vapor stream of column 60B, and returned to the column as stream 6013. The bottoms 6015, preferably containing highly pure ethanol, may be processed in an ethanol dehydration unit 60E and then may be processed in a post-distillation treatment unit 60H, to remove sulfur compounds, from which may emerge the final ethanol product 6022. In one embodiment, an ethanol condensate 6100 from the ethanol drying unit 60E may be passed to the inlet to the methanol-ethanol/heavies separator 60B.

The methanol/methyl acetate stream 6011 may be passed to a methanol/methyl acetate separator 60F where methanol and methyl acetate up to the methanol/methyl acetate azeotrope may be separated and may be stored in methanol storage unit 60G. In one embodiment, methanol 6039 may be recycled to the ethanol reactor in the alcohol synthesis unit 50. The methyl acetate stream 6033 may in one embodiment be vaporized in a fusel oil vaporizer 60J and fed to the gasification unit 20, preferably to a TRC, where it may be partially oxidized forming carbon monoxide, hydrogen, carbon dioxide, and some water. The heat required to vaporize fusel oil streams 6033 and/or 6026 may in vaporizer 60J may in one embodiment be obtained from the outlet 6017 of the ethanol dehydration unit 60E.

In one embodiment, at least a fraction of methanol 6039 may be sent to an auto-thermal reformer (ATR) for creation of syngas for further use in the overall process. In one embodiment, only the excess methanol which cannot be recycled to alcohol synthesis reactor will be sent to the ATR. In another embodiment, at least a fraction of methanol 6039 may be sent back to the vicinity of the outlet of gasification unit 20 (preferably the outlet of a TRC), and used to quench the hot syngas resulting from syngas generation.

An ATR may in one embodiment be used to modulate the $H_2$:CO ratio in the syngas of the ethanol reactor. In one embodiment, alcohols, preferably all alcohols in the system other than ethanol and methanol, and most preferably propanol, may be fed into the ATR. Steam may be injected into the syngas to provide water for a water-gas shift reaction that may take place in the ATR. The ATR may also be fed by an oxygen stream 1132. In one embodiment, the ATR may also be fed by a natural gas or methane stream. Thus, in an optional mode of operation, the ATR may operate by reforming methane with carbon dioxide produced as part of the water-gas shift reaction. This mode of operation may be referred to as an augmentation step, and may be useful in many situations, such as when there is a shortage of syngas, when the gasifier or other syngas production facility goes down, or when there is a need for more hydrogen. Optionally, the ATR may be supplied with a carbon dioxide line to provide carbon dioxide if necessary to balance the amount of natural gas. Such carbon dioxide might, in one embodiment, be obtained from another part of the overall process, such as stream 5015 of FIG. 7.

Figure 10:
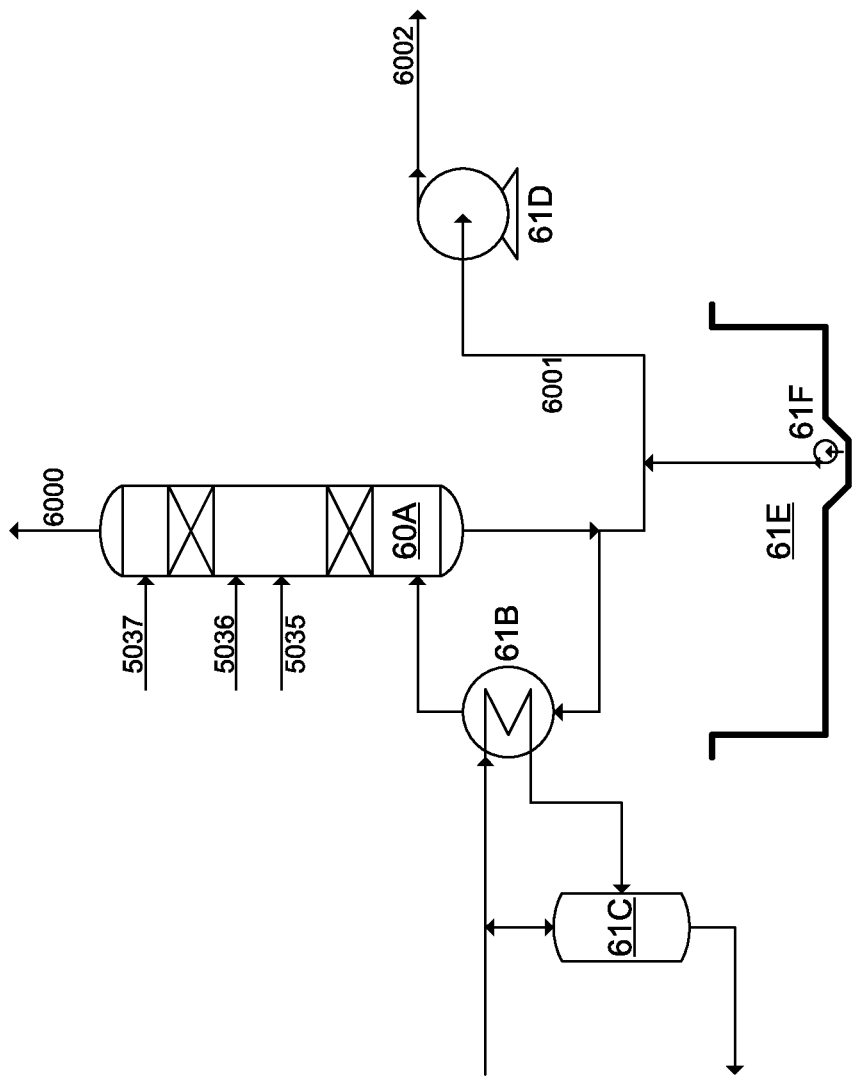
FIG. 10 shows an illustration of one embodiment of a mixed alcohol degasser for use with the present disclosure.

FIG. 10 shows an illustration of one embodiment of a mixed alcohol degasser 60A. The mixed alcohol liquid stream 5035, which may have been preheated as discussed above, may be sent to the mixed alcohol degasser 60A, while flash gas 5036 may also flow to degasser 60A optionally through a separate route. The degasser column may preferably be provided with two packed sections where both the flash gas 5036 and mixed alcohol liquid stream 5035 may preferably enter the column between the packed sections. The lower packed section, if used, may strip the remaining dissolved gases 6000 from the mixed alcohol stream. The reboil heat may in one embodiment be provided by condensing steam in a mixed alcohol degasser reboiler 61B to maintain the desired temperature at the bottom of the column. The steam condensate may be collected in a degasser reboiler steam condensate drum 61C and then may be sent to a condensate flash drum. A mixed alcohol degasser bottoms pump 61D may transfer the degassed mixed alcohol stream 6002 from the bottom of the degasser column to an ethanol/heavies column (e.g., 60B of FIG. 9).

The upper packed section of the degasser column may preferably utilize a water stream 5037 to absorb the majority of the alcohol compounds that may be present in the combined vapor stream comprising the flash gas 5036 entering the column and the stripping vapor from the bottom section. As discussed above, the water "reflux" stream 5037 may be supplied to the top of the degasser 60A by a small slipstream from a discharge from the alcohol synthesis area 50, and in one embodiment from absorber water feed pump 50S (FIG. 7). The water from stream 5037 may in one embodiment originate from stream 6029 as the water components separated from the propanol/water separator 60C (FIG. 9). As discussed above, the overhead vent gas 6000 from the degasser 60A may in one embodiment be recycled the syngas cleanup and compression unit 40.

All process liquids drained from equipment and piping from the area may preferably be collected in an alcohol drain sump drum 61E. The drum may in one embodiment be vented to the flare header, and may preferably have a continuous nitrogen purge. An alcohol drain sump drum pump 60F may be utilized to intermittently pump the recovered liquid into the suction line 6001 of the mixed alcohol degasser bottoms pump 61D.

Figure 11:
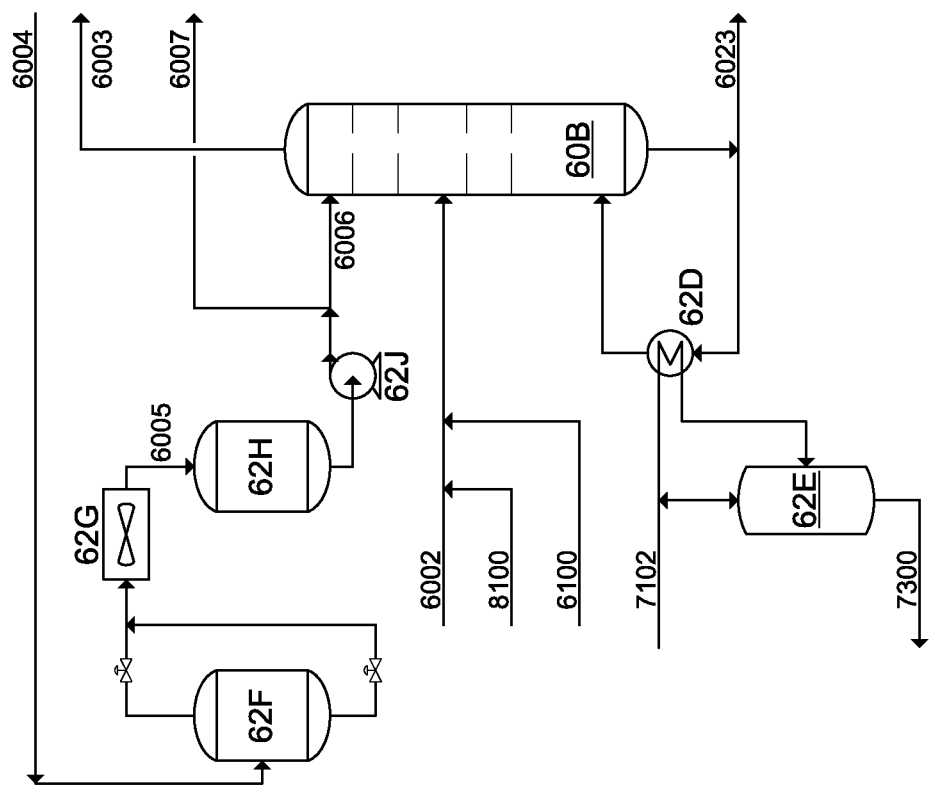
FIG. 11 shows an illustration of one embodiment of an ethanol/heavies separator for use with the present disclosure.

FIG. 11 shows an illustration of one embodiment of an ethanol/heavies separator 60B, together with possible related elements. A mixed alcohol stream 6002 may preferably be fed directly to the methanol-ethanol/heavies column 60B where ethanol and lighter components (e.g., methanol) 6003 may be separated from propanol and heavier components (e.g., heavy alcohols and water) 6023. The column may also preferably receive a small amount of condensate 6100 recycled from ethanol drying unit 60E. Additionally, when there is a requirement to recycle off-spec ethanol from storage, an off-spec stream 8100 may combine with the hot mixed alcohol stream before entering the ethanol/heavies column 60B. The reboil heat may be provided to the column by condensing steam 7102 in an ethanol/heavies column reboiler 62D to maintain the desired temperature at the bottom of the column. Steam condensate may be collected in an ethanol/heavies column reboiler steam condensate drum 62E and then, in one embodiment, sent to a condensate flash drum via 7300.

Figure 13:
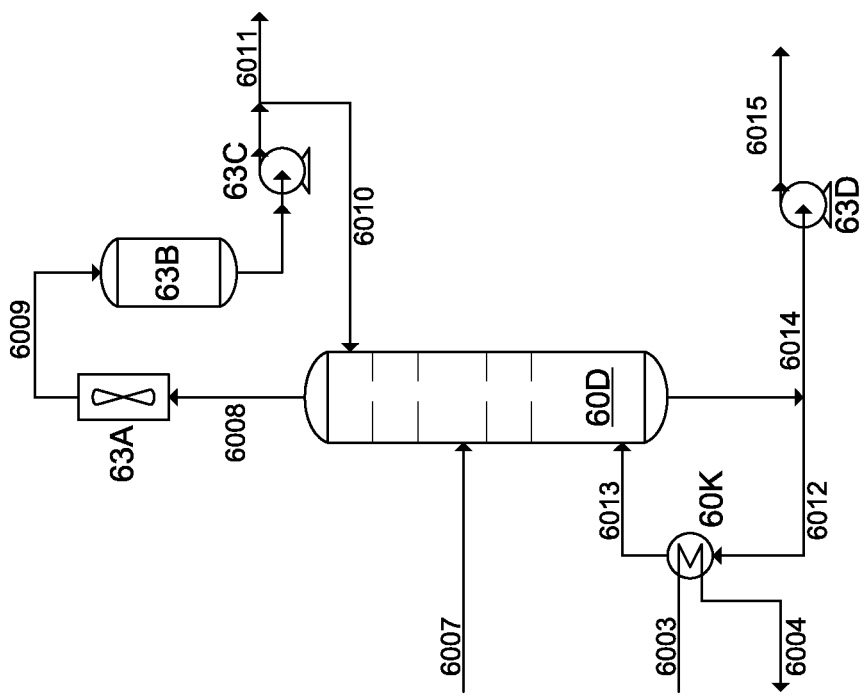
FIG. 13 shows an illustration of one embodiment of a methanol/ethanol separator for use with the present disclosure.

An ethanol/methanol vapor mixture 6003 may exit the top of the column and may, in one embodiment, provide reboil heat to a downstream methanol/ethanol column 60D (FIG. 9, FIG. 13). A partially condensed stream 6004 may be sent to an ethanol/heavies column flash drum 62F where the vapor and liquid may be separated to avoid problems with vertical two-phase flow. The vapor stream from the drum may in one embodiment flow through a control valve that may be adjusted to maintain the desired pressure at the top of the column and the liquid stream may exit the drum on level control. The vapor and liquid streams may then be recombined close to the inlet of an ethanol/heavies column trim condenser 62G where the remainder of the overhead vapor may in one embodiment be condensed by heat exchange with ambient air. The outlet temperature from the condenser is preferably controlled by automatic adjustment of the air outlet louvers. The completely condensed overhead stream 6005 may then flow to an ethanol/heavies column reflux drum 62H. The reflux stream 6006 may then be returned to the top of column 60B by an ethanol/heavies column reflux pump 62J on flow control. An overhead ethanol/methanol liquid product 6007 may also flow through the reflux pump 62J and be sent to the Methanol/Ethanol Column 60D (FIG. 9, FIG. 13) on level control.

A propanol and heavier (e.g., heavy alcohols and water) stream 6023 may leave the bottom of column 60B on level control and flow to a propanol/water column 60C. In order to accommodate the potential need to recycle off-spec ethanol product through the purification unit 60, the methanol-ethanol/heavies column and its associated equipment may preferably be designed for an additional capacity above the normal plant design rate.

Figure 12:
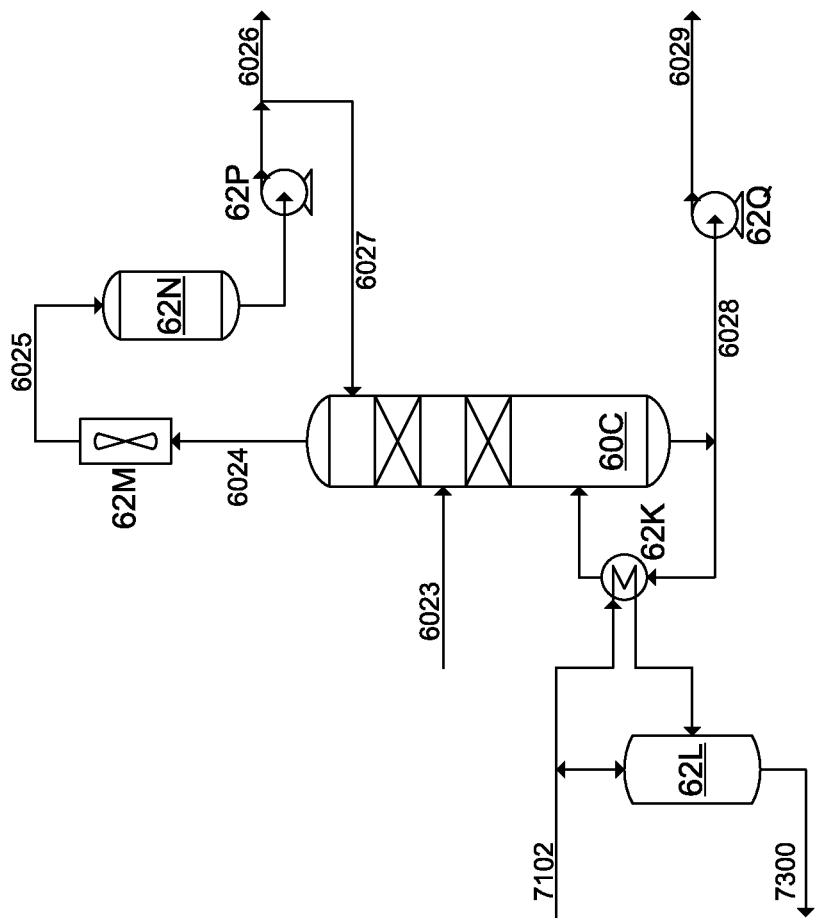
FIG. 12 shows an illustration of one embodiment of a propanol/water separator for use with the present disclosure.

FIG. 12 illustrates one embodiment of a propanol/water separator 60C and possible related elements. A propanol/water column 60C may preferably receive a propanol and heavier (e.g., heavy alcohols and water) stream 6023 directly from the bottom of a methanol-ethanol/heavies column 60B. Column 60C may be designed to separate propanol and heavier hydrocarbons from any recyclable absorbent water. Reboil heat may be provided to the column by condensing steam 7102 in a propanol/water column reboiler 62K to maintain the desired temperature at the bottom of the column. The steam condensate may be collected in a propanol/water column reboiler steam condensate drum 62L and then in one embodiment sent to a condensate flash drum via 7300.

A vapor from column 60C, which may comprise propanol, may exit the top of the column and be condensed in a propanol/water column condenser 62M, preferably by heat exchange with ambient air. The outlet temperature of vapor 6025 from the condenser may in one embodiment be controlled by automatic adjustment of the air outlet louvers. An overhead stream 6025, which is preferably completely condensed, may then flow to a propanol/water column reflux drum 62N. The pressure at the top of column 62C may be automatically maintained by adjusting a control valve in outlet line 6025 from the condenser. The pressure in reflux drum 62N may be automatically maintained in various ways, including by either adjusting a hot vapor bypass valve around the condenser or venting non-condensable gases that accumulate in the drum to a relief header. Reflux 6027 may be returned to the top of column 62C by a propanol/water column reflux pump 62P, which may be on flow control. An overhead liquid, which in one embodiment may comprise predominantly propanol and other fusel oils, may flow through the reflux pump 62P and be sent (6026) to a fusel oil vaporizer 60J (see FIG. 9) to preferably completely vaporize the stream before it is preferably recycled back to the gasification unit 20 (and preferably to a TRC within the gasification unit).

A regenerated recycle water stream 6028 may leave the bottom of column 60C and be pumped by a recycle water pump 62Q as stream 6029 to the alcohol synthesis unit 50, as discussed above, for eventual for reuse in a mixed alcohol absorber 50L (see FIG. 7).

FIG. 13 illustrates one embodiment of a methanol/ethanol separator 60D and associated elements. A methanol/ethanol column 60D may receive an ethanol/methanol stream 6007. The column may preferably be designed to separate methanol and other light components from the ethanol product. As mentioned earlier, hot overhead vapor 6003 from an ethanol/heavies column 60B may in one embodiment be used to reboil the liquid product 6012 from column 60D column in methanol/ethanol column reboiler 60K (returning to the column as stream 6013). In one embodiment, varying the amount of the hot vapor bypassing the reboiler may provide temperature control for the bottom of the column. This heat integration between the two columns is preferable to conserve steam that would otherwise be required for the reboil heat.

A vapor 6008, preferably predominately methanol, may exit the top of column 60D and be condensed in a methanol/ethanol column condenser 63A by heat exchange with ambient air. The outlet temperature from the condenser may be controlled by automatic adjustment of the air outlet louvers. The preferably completely condensed overhead stream 6009 may then flow to a methanol/ethanol column reflux drum 63B. The pressure at the top of the column may preferably be automatically maintained by adjusting a control valve in the outlet line from the condenser. The pressure in the reflux drum 63B may be automatically maintained in many ways, including by either adjusting a hot vapor bypass valve around the condenser or venting non-condensable gases that may accumulate in the drum to a relief header. Reflux 6010 may be returned to the top of the column by a methanol/ethanol column reflux pump 63C on flow control. The overhead liquid may also flow through the reflux pump 63C and be sent (via 6011) to a methanol/methyl acetate column 60F.

An ethanol product stream 6014 may leave the bottom of the column and be pumped for further processing by the ethanol pump 63D. In order to accommodate the potential need to recycle off-spec ethanol product 8100 through purification unit 60, the methanol/ethanol column 60D and its associated equipment may preferably be sized and designed for additional capacity above the normal plant design rate.

Figure 14:
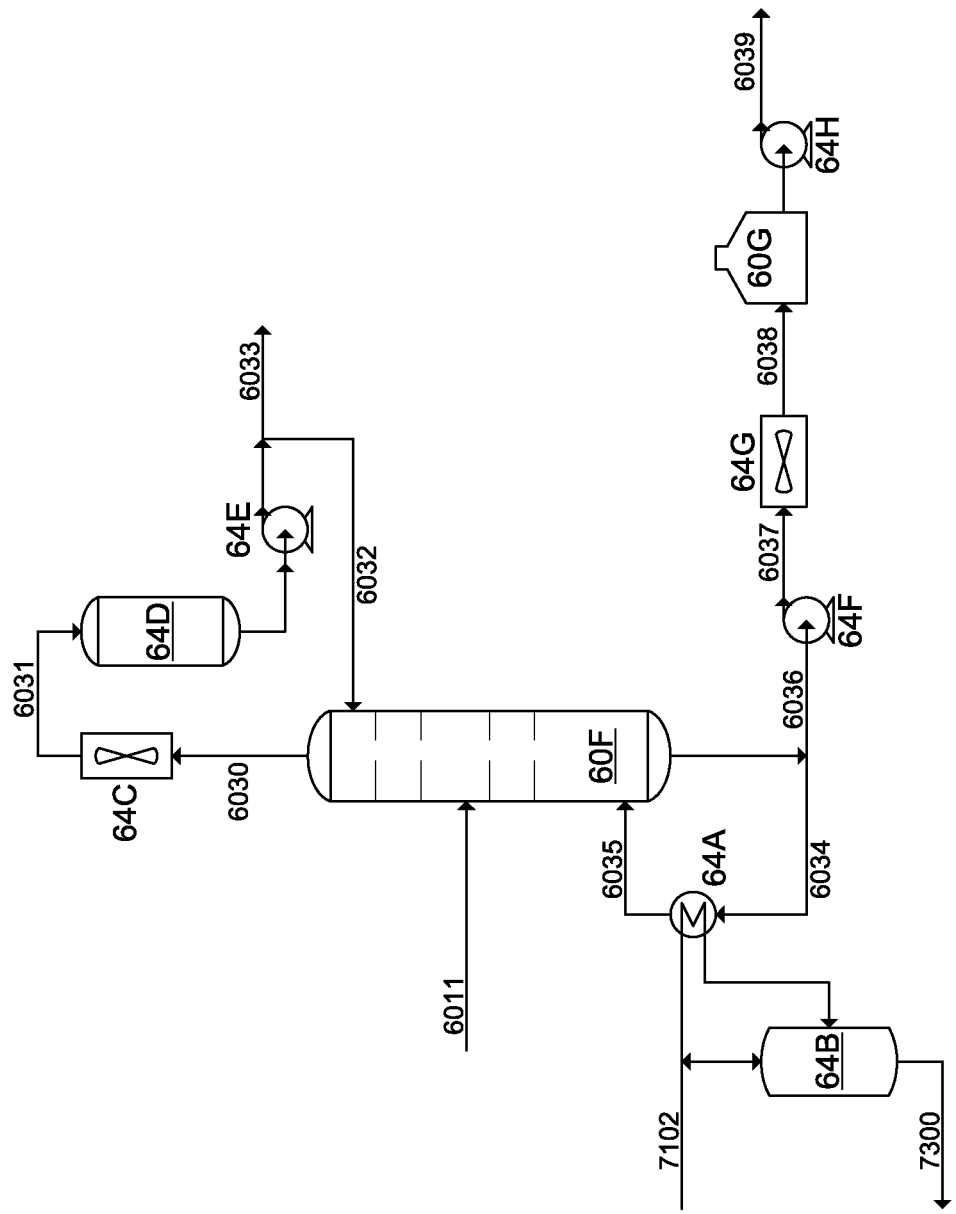
FIG. 14 shows an illustration of one embodiment of a methanol/methyl acetate separator for use with the present disclosure.

FIG. 14 shows an illustration of one embodiment of a methanol/methyl acetate separator 60F, methanol storage unit 60G, and associated units. A methanol/methyl acetate column 60F may receive a stream 6011, which is preferably predominantly methanol. The column 60F may preferably be designed to remove methyl acetate from the methanol stream so that the methanol may preferably be recycled to the gasification unit 50. The reboil heat may be provided to the column by condensing steam 7102 in a methanol/methyl acetate column reboiler 64A to maintain the desired temperature at the bottom of the column. A steam condensate may be collected in a methanol/methyl acetate column reboiler steam condensate drum 64B and then sent to a condensate flash drum (via 7300).

A predominately methyl acetate vapor 6030 may exit the top of the column and be condensed in a methanol/methyl acetate column condenser 64C by heat exchange with ambient air. The outlet temperature from the condenser may be controlled in one embodiment by automatic adjustment of the air outlet louvers. An overhead stream, which may preferably be completely condensed, may then flow to a methanol/methyl acetate column reflux drum 64D. The pressure at the top of the column is automatically maintained by adjusting a control valve in the outlet line from the condenser. The pressure in the reflux drum is automatically maintained by either adjusting the hot vapor bypass valve around the condenser or venting non-condensable gases that accumulate in the drum to the relief header. Reflux 6032 may be returned to the top of the column by a methanol/methyl acetate column reflux pump 64E on flow control. An overhead liquid 6033, which is preferably predominantly methyl acetate, may also flow through reflux pump 64E and be combined with fusel oil, preferably to sent to the gasification unit 20.

A methanol stream 6036 may exit the bottom of the column and be pumped by a methanol/methyl acetate column bottoms pump 64F then conveyed (6037) through a methanol cooler 64G where it may be cooled by exchange with ambient air and then sent (6038) to a methanol storage tank 60G. The outlet temperature from the cooler may preferably be controlled by automatic adjustment of the air outlet louvers.

A methanol storage tank 60G may receive a cooled methanol stream 6038. The tank may be blanketed with nitrogen to prevent air from migrating into the tank. Any vapors that may leave the tank as it is being filled may be vented to the atmosphere at a safe location. The methanol 6039 may preferably then be pumped by a methanol recycle pump 64H to alcohol synthesis unit 50 where it may combine with the syngas stream prior to an inlet of a reactor (see, e.g., FIG. 7).

Figure 15:
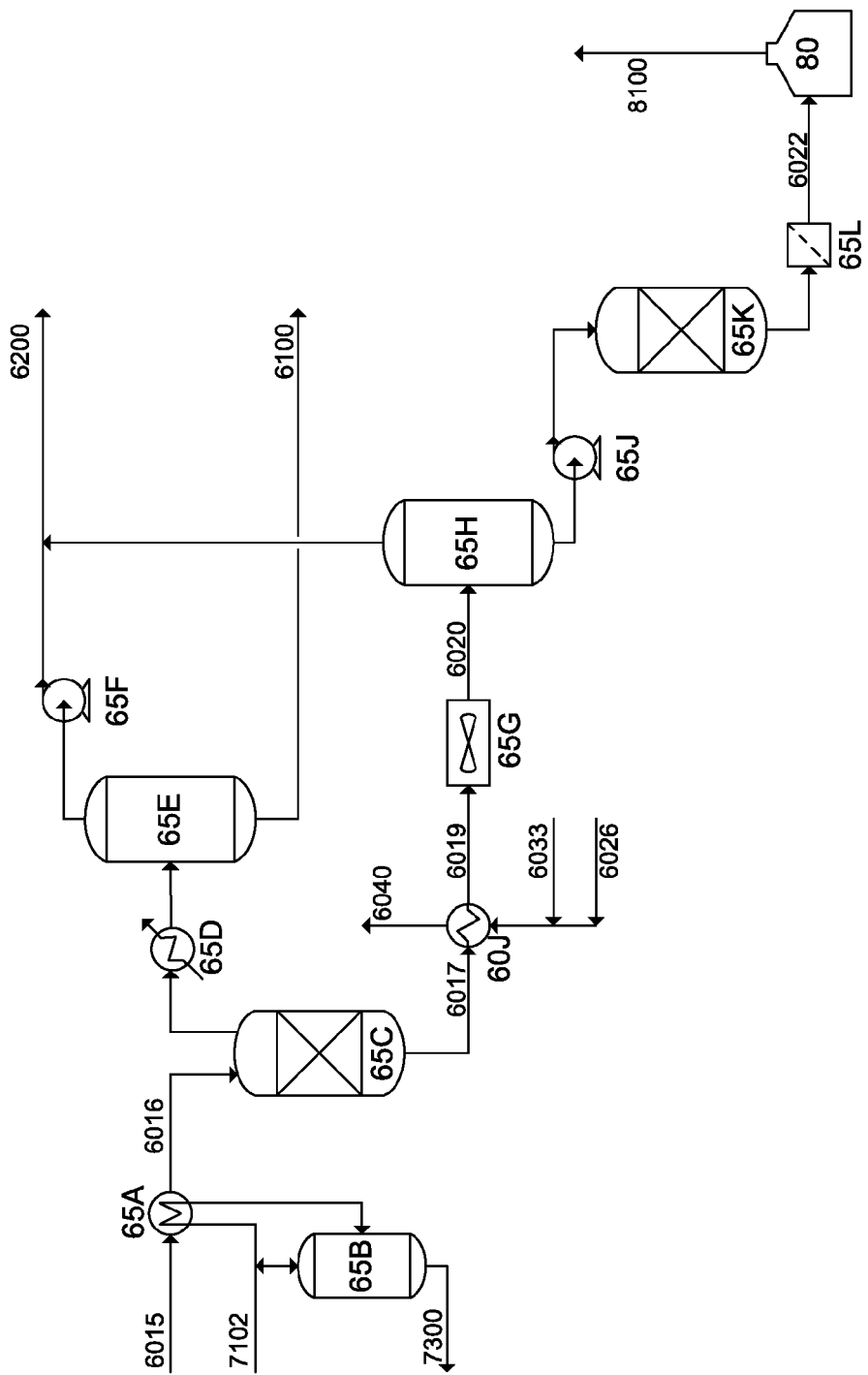
FIG. 15 shows an illustration of one embodiment of an ethanol drying and sulfur removal unit for use with the present disclosure.

FIG. 15 illustrates one embodiment of a sulfur removal unit 60H, and ethanol storage and handling unit 80, and related elements. After being pumped from the bottom of a methanol/ethanol column (e.g., 60D), an ethanol liquid 6015 may flow through an ethanol vaporizer 65A where it may be vaporized and superheated by condensing steam 7102. The steam condensate 7300 may be collected in an ethanol dryer vaporizer steam condensate drum 65B and then sent (7300) to a condensate flash drum. The ethanol vapor 6016 then may flow through one or more ethanol dryers 65C to remove water in the stream to meet the desired ethanol product specification. Two or more ethanol dryers may preferably be provided in order to have at least one dryer in operation and at least one dryer in regeneration mode. In one embodiment, the overhead of ethanol dryer 65C may be condensed and then recycled to a point upstream in the purification unit 60. Preferably, the overhead may be cooled in exchanger 65D, preferably by cooling water, then separated into a vapor and liquid in a flash drum 65E. The vapor may be pumped (65F), preferably to flare 6200. The liquid 6100 may preferably be recycled to a point upstream of ethanol/heavies separator 60B.

Following dehydration the ethanol vapor may in one embodiment be passed over a sorbent such as SULFATREAT SELECT ULTRA (provided by M-I SWACO), or activated carbon in another embodiment, to adsorb various organic sulfur compounds including sulfides, di-sulfides and mercaptans. This post distillation treatment system may reduce the total sulfur in the ethanol product stream sufficiently to meet ASTM product purity requirements.

Dry ethanol vapor 6017 may in one embodiment be used to vaporize fusel oil in the fusel oil vaporizer 60J, as discussed earlier. Preferably, final condensing and cooling of the ethanol product 6019 occurs in an ethanol condenser 65G by heat exchange with ambient air. The temperature in the outlet 6020 from the condenser may preferably be controlled by automatic adjustment of the air outlet louvers.

The cooled ethanol product liquid 6020 may flow to an ethanol product receiver 65H that may preferably operate under a nitrogen blanket and preferably vent (6200) to a flare header on high pressure. Ethanol may then be pumped from the receiver by an ethanol product transfer pump 65J to one or more sulfur adsorbent beds 65K for the removal of trace sulfur compounds. In one embodiment, two adsorbent beds may be piped in a lead/lag configuration to allow for on-line replacement of spent adsorbent. The treated ethanol product may then flow through an ethanol filter 65L to remove any adsorbent fines from the product stream before it is routed to ethanol storage and treatment unit 80.

In order to accommodate the potential need to recycle off-spec ethanol product through purification unit 60, the components of the purification unit 60 may preferably be designed for an additional capacity above the normal plant design rate.

Ethanol storage and treatment unit 80 may include at least one or more vessels for storing ethanol, facilities to allow product testing and measurement, preferably with pumps and valves configured to allow the recycling of off-spec ethanol 8100 back to purification 60.

Electricity Generation

Figure 16:
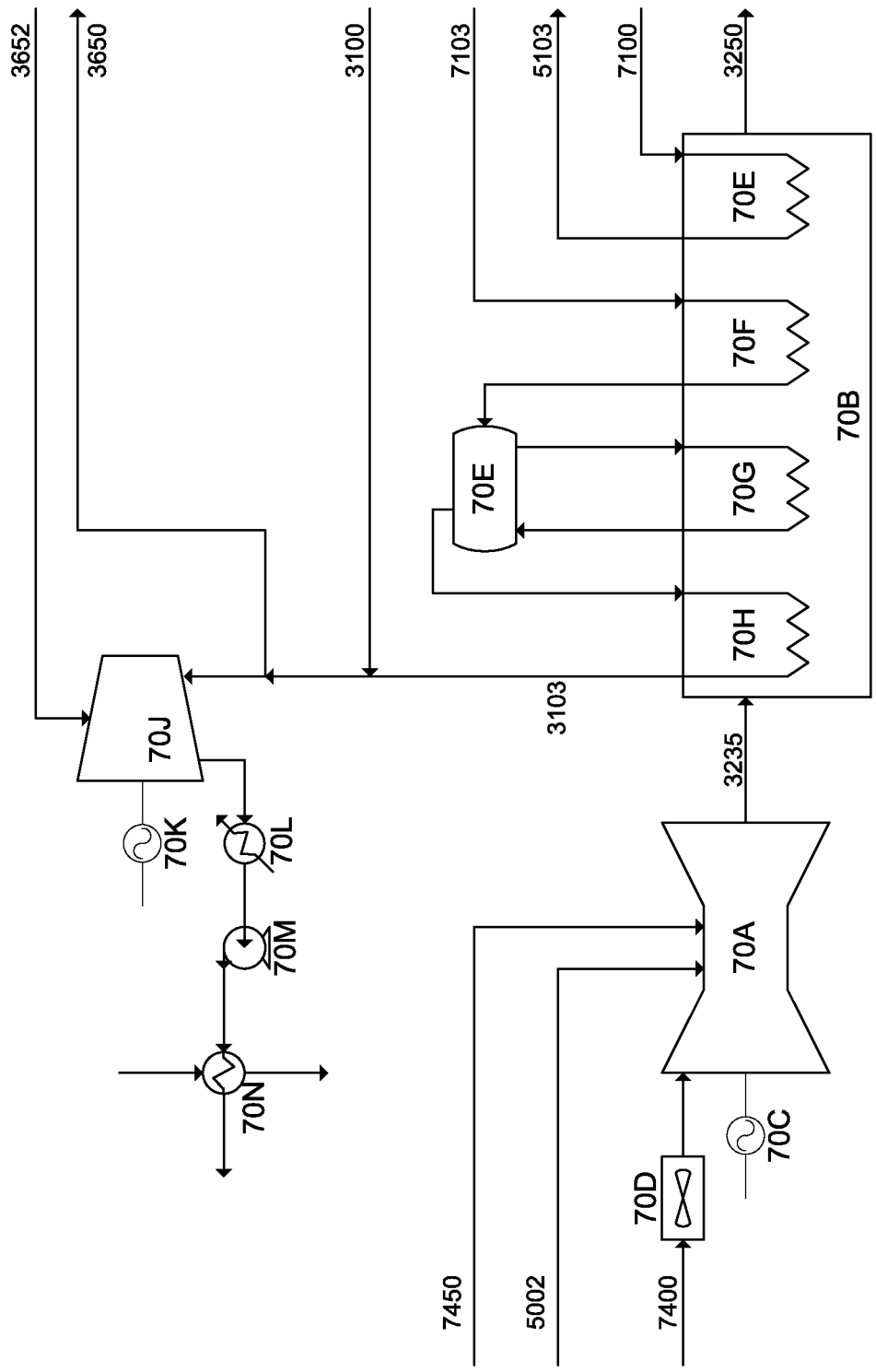
FIG. 16 shows one embodiment of an electricity generation unit for use with the present disclosure.

FIG. 16 illustrates one embodiment of an electricity generation unit 70 which may generate electricity from steam, natural gas, and/or syngas. In the alcohol synthesis unit 50, in one embodiment approximately 15% of the syngas (5002) may be combusted with air 7400 in combustion turbine 70A. In a preferred embodiment, natural gas 7450 is also used in addition to syngas 5002 as fuel for gas turbine 70A. The combustion turbine may be linked to a generator 70C that may produce power for the plant. During normal operation, the combustion turbine may preferably be designed to operate fully loaded to maximize power generation. Turbine exhaust gas 3235 may flow through a gas turbine heat recovery steam generator (HRSG) 70B to recover heat from the hot gas stream by, in one embodiment, (70E) preheating high-pressure boiler feed water 7100 for one or more reactors (via 5103) in the alcohol synthesis unit 50, (70F) preheating the medium-pressure boiler feed water 7103 supply to the HRSG steam drum 70E, (70G) generating saturated steam preferably at about 800 psig and (70H) superheating the preferably about 55.2 bar (about 800 psig) steam it produces 3103. After flowing through the HRSG, the cooled exhaust gas 3250 may preferably be vented to the atmosphere through a vent stack.

The steam drum 70E may preferably be supplied with continuous and/or intermittent blowdown facilities to maintain the water quality. The continuous and/or intermittent blowdown streams may preferably be routed separately to blowdown drums.

All of the preferably 55.2 bar (800 psig) steam 3100 that may be superheated in the waste heat recovery unit 30, and all the steam 3103 that may be generated in the gas turbine HRSG 70A, may preferably be sent to the steam turbine 70J and generator 70K to generate power. However, in one embodiment, a portion of the steam 3650 may first pass through a heater (e.g., 50G of FIG. 7) upstream of an alcohol synthesis reactor in the alcohol synthesis unit 50, before returning as stream 3652 and entering the steam turbine 70J at an interstage. The steam turbine 70J may in one embodiment operate as a total condensing turbine utilizing (1) a steam turbine condenser 70L, (2) a steam turbine condenser hot well pump 70M, and (3) a steam turbine after condenser 70N which may preferably use blowdown and/or other waste water from various parts of the overall process as coolant. The clean condensate from the after condenser may preferably be sent directly to a plant deaerator and then reused in various parts of the facility.

Reactor Configuration and Chemistry

Alcohol synthesis reactors (e.g., 50H in FIG. 7) for use in this disclosure may take many forms consistent with the claims defined herein. In a preferred embodiment, two ethanol synthesis reactors 50H may be provided with each train consisting of two reactors in series, for a total of four reactors. Preferably, the reactors are packed bed tubular reactors containing a moly-sulfide catalyst. Each reactor train may be sized for 50% of the total design syngas rate. In each reactor, the syngas may contact catalyst as it flows down through the tubes inside of the reactor.

Any suitable catalytic reactor may be used. In some embodiments the reactor may include a plurality of tubes filed with one or more mixed alcohol catalysts. In an exemplary embodiment, the reactor may be in a vertical downflow configuration with a plurality of elongated, 2-inch (5.08 cm) outer diameter tubes filed with the catalyst.

Table 2 presents the design and operating parameters for one illustrative embodiment of one of the reactors.

TABLE 2

Approximate design parameters for an ethanol reactor in one illustrative embodiment of the disclosure.

| | |
|---|---|
| Gas Hourly Space Velocity | 4000 hr$^{-1}$ |
| Reactor Diameter | 3.81 meters |
| | (12.5 feet) |
| Catalyst Depth in Tubes | 6.096 meters |
| | (20 feet) |
| Number of Tubes | 2440 |
| Tube Diameter | 5.08 cm O.D. |
| | (2" O.D.) |
| Tube Side Outlet Temperature | 350° C. |
| | (662° F.) |
| Tube Side Operating Pressure | 103.4 bar |
| | (1500 psig) |
| Shell Side Operating Temperature | 254-271° C. |
| | (489-520° F.) |
| Shell Side Operating Pressure | 82.7-103.4 bar |
| | (1200-1500 psig) |

In the reactor(s), the following water gas shift reaction may occur:

$$CO + H_2O \leftrightarrow CO_2 + H_2$$

The water gas shift reaction is slightly exothermic in the direction of producing carbon dioxide and hydrogen. In addition, reactor conditions may be provided so that some or all of the following catalyzed reactions occur:

$$CO + 3H_2 \rightarrow CH_4 + H_2O \quad \text{(methane)}$$

$$2CO + 5H_2 \rightarrow C_2H_6 + 2H_2O \quad \text{(ethane)}$$

$$CO + 2H_2 \rightarrow CH_3OH \quad \text{(methanol)}$$

$$2CO + 4H_2 \rightarrow C_2H_5OH + H_2O \quad \text{(ethanol)}$$

$$3CO + 6H_2 \rightarrow C_3H_7OH + 2H_2O \quad \text{(propanol)}$$

$$3CO + 4H_2 \rightarrow CH_3COOCH_3 + H_2O \quad \text{(methyl acetate)}$$

Other reactions may also occur, and some of the reactions listed above can go in both directions depending on the various equilibrium conditions.

While the gasification reaction in the gasification unit 20 may create one hydrogen molecule for every carbon monoxide molecule, the production of ethanol requires twice as many hydrogen molecules as carbon monoxide molecules. The additional hydrogen may be produced in the water gas shift reaction, at the expense of producing carbon dioxide. In the preferred embodiment, carbon dioxide may be removed from the process through a separation unit such as the solvent system 50A (shown in FIG. 7). The removal of carbon dioxide from the stream passing through the reactor(s) may push the equilibrium of the water gas shift reaction in favor of producing hydrogen, which in turn may result in the production of more ethanol.

As discussed above, in some embodiments, to maximize the production of ethanol from syngas, unconverted syngas and methanol may be recycled from the purification unit 60 to a point upstream of the alcohol synthesis reactor(s). This methanol may be converted to ethanol in the reactor(s) by the following reaction:

$$CH_3OH + CO + 2H_2 \rightarrow C_2H_5OH + H_2O.$$

In addition, propanol and higher alcohols, as well as methyl acetate, may be recycled to the gasification unit 20 and may be cracked to produce additional syngas.

Methane, ethane, and other light gases may also be produced in the reactor(s). At least some of these light gasses may be recycled with the unreacted syngas. In one embodiment, at least some of these gases may be purged from the main reactor loop by diversion of a portion of the syngas to a combustion turbine 70A for use in generating electricity. In another embodiment, at least some of the methane and/or ethane may be reformed by, for example, the use of an autothermal reformer, according to the following reactions:

$$2CH_4 + O_2 + CO_2 \rightarrow 3H_2 + 3CO + H_2O$$

$$C_2H_6 + O_2 + CO_2 \rightarrow 2H_2 + 3CO + H_2O.$$

In another embodiment, at least some of the methane, ethane, and other light gases may follow the methanol through purification unit 60, and may be recycled to the reactor(s) with the methanol. In another embodiment, at least some of the methane, ethane, and other light gases may be separated from recycle syngas through a separator dedicated for that purpose. An overall process may make use of any or all of the above alternative embodiments simultaneously. In yet another embodiment, methane, ethane, and other hydrocarbons may be converted to syngas in a catalytic reformer downstream of the gasification unit 20, by means known in the art.

The heat released from the various reactions in the alcohol synthesis reactor(s) may be transferred to water, preferably on a shell side of the reactor(s). Preferably, this water may be flashed to steam as described above. Additional heat and energy may be recovered from the reactor effluent, as described above.

Certain reactor conditions may have a direct impact on the yield of ethanol formed from syngas in catalytic alcohol synthesis processes such as those described in the present disclosure. The reactions occurring in the alcohol synthesis reactor(s) may be equilibrium reactions at a given set of conditions. By manipulating certain reactor conditions, these reactions can either move to form more complex or less complex molecules.

More specifically, it has been determined there are a number of synthesis reactor conditions which may have a direct impact on the yields of ethanol and other alcohols. These conditions may include any one or more of: partial pressures of reactants, diluents, temperature, pressure, gas hourly space velocity (GHSV) and the amount of methanol recovered in the effluent from the reactor and recycled back to the reactor. Without being bound by any particular theory, it is useful to consider methanol to be a building block for the production of ethanol, and to consider ethanol in turn to be a building block for higher alcohols.

In one exemplary and non-limiting embodiment, at a specific temperature and pressure, if the gas hourly space velocity (GHSV) is increased, the molar ratio and mass yields of the synthesis reaction products can be selectively controlled such that formation of methanol and/or ethanol may be increased, and formation of the heavier alcohols may be decreased.

It is most useful to consider GHSV, temperature, and pressure to the be the primary determinants of reactor efficiency and productivity, rather than the volume of catalyst. Surprisingly, one may achieve essentially the same performance of an alcohol synthesis reactor over a wide range of catalyst volumes. Thus, it may be possible to minimize the amount of catalyst volume and therefore save cost.

In some embodiments, the GHSV may be at or above about 2,000 $hr^{-1}$. In other embodiments, the GHSV may be in the range of about 2,000 to 10,000 $hr^{-1}$ or higher, or preferably within the range of about 3,000 to about 7,000. The reactions that convert syngas components to alcohol compounds are exothermic and may cause the temperature of the syngas to increase as it flows through the catalyst. In one embodiment, the syngas may enter the first reactor in each train at about 315.5° C. (about 600° F.) and the temperature of the reactants may be allowed to increase to about 350° C. (662° F.). In other embodiments, the core temperature of the catalyst may be in a range of about 315.5° C. to about 371° C. (600° F. to about 700° F.). The pressure may preferably be about 103.5 bar (about 1500 psig), or within a range such as 68.9 to 137.9 bar (1000 to 2000 psig). The GHSV, temperature, and pressure may be optimized, or further optimized from the ranges described above, to achieve the desired CO conversion and ethanol selectivity.

In some embodiments, methanol may be introduced along with syngas into the reactor inlet to increase the formation of ethanol from the reaction of hydrogen and carbon monoxide. In an exemplary embodiment, the molar ratio of hydrogen to carbon monoxide ($H_2:CO$) in the reactor inlet stream may be in the range of about 0.7:1 to about 2.0:1, more preferably approximately 1.5:1. In embodiments where two or more reactors are used and configured in series, methanol may be feed to one or more of the reactors by injecting methanol between the reactors.

In one embodiment, the ethanol reactor(s) may convert syngas into ethanol utilizing a catalyzed thermochemical conversion. Examples of suitable catalysts are described in WO 2009/009389 A2 (published Jan. 15, 2009) and WO 2009/009388 A2 (published Jan. 15, 2009), which are incorporated herein by reference in their entirety. Preferably, the reactor(s) may use a catalyst that may convert methanol to ethanol and higher alcohols, or that may convert syngas and/or methanol selectively into ethanol. Suitable catalysts that may promote the formation of ethanol and/or higher alcohols are also known in the art, and may for example include $ZnO/Cr_2O_3$, $Cu/ZnO$, $Cu/ZnO/Al_2O_3$, $CuO/CoO$, $CuO/CoO/Al_2O_3$, $Co/S$, $Mo/S$, $Co/Mo/S$, $Rh/Ti/SiO_2$, $Rh/Mn/SiO_2$, $Rh/Ti/Fe/Ir/SiO_2$, $Rh/Mn/MCM-41$, $Ni/S$, $Ni/Mo/S$, $Ni/Co/Mo/S$ and any of the foregoing in combination with Mn and/or V. The catalyst may also include one or more basic promoters, such as potassium, alkaline-earth, and rare-earth metals.

Sulfided catalysts have many advantages known in the art, including the advantage of being sulfur-tolerant, which may reduce the cost of cleaning the syngas upstream of the reactor. In a preferable embodiment, the reactor(s) use a may use a $CoS_i/MoS_i/NiS_i$ catalyst. In one embodiment, the catalyst charged to the reactor(s) may contain about 12-16 wt. % Mo, about 1-2 wt. % Ni, about 4-6 wt. % Co, and about 6-8 wt. % potassium, with the remainder being activated carbon. Preferably, the catalyst may contain about 14 wt. % Mo, about 1.5 wt. % Ni, about 4.5 wt. % Co, and about 7.2 wt. % potassium, with the remainder being activated carbon. The catalyst may preferably be sulfidized by injecting a sulfur donor compound such as $H_2S$ or dimethyl sulfide into the syngas stream that passes through the reactor(s). Sulfidization may preferably occur on a continuous basis. Production and use of a suitable class of $CoS_i/MoS_i/NiS_i$ catalysts is described in U.S. Provisional Application No. 61/159,780 (filed Mar. 12, 2009) and applications claiming priority thereto.

In one embodiment, reactors using different catalysts may be joined in series, or a single reactor may have different zones containing different catalysts. For example, a reactor containing a catalyst that promotes the formation of methanol may precede a reactor containing a catalyst that promotes the formation of ethanol and/or higher alcohols from methanol. The entire reactor may also, in one embodiment, comprise the latter catalyst. Thus, an embodiment may comprise a methanol catalyst and a mixed alcohol catalyst arranged in series, among other possible arrangements, or two mixed alcohol catalysts arranged in series. Suitable catalysts that may promote the formation of methanol are known in the art, and may for example include $ZnO/Cr_2O_3$, $Cu/ZnO$, $Cu/ZnO/Al_2O_3$, $Cu/ZnO/Cr_2O_3$, $Cu/ThO_2$, $Co/S$, $Mo/S$, $Co/Mo/S$, $Ni/S$, $Ni/Mo/S$, $Ni/Co/Mo/S$, and any of the foregoing in combination with Mn and/or V. The catalyst may also include one or more basic promoters, such as potassium, alkaline-earth, and rare-earth metals, but such promoter may also be omitted to increase selectivity toward methanol.

In one embodiment, the alcohol synthesis unit 50 may comprise two reactors in series. Preferably, methanol 6039 may be injected into a mixing point between the two reactors, so that the recycle methanol bypasses the upstream reactor and combines with syngas to flow into the downstream reactor. The catalyst in each of the two reactors may be the same, or each reactor may have a different catalyst. In an alternate embodiment, instead of two separate reactors, the alcohol synthesis unit 50 may comprise two reaction zones within a single reactor, and methanol may be injected into a space between the two reaction zones.

Exemplary embodiments have been described with reference to specific configurations. The foregoing description of specific embodiments and examples of the invention have been presented for the purpose of illustration and description only, and although the invention has been illustrated by certain of the preceding examples, it is not to be construed as being limited thereby.

What is claimed is:

1. A method for converting organic materials into ethanol comprising:
separating non-organic materials from a solid feedstock which may optionally contain entrained liquids, thereby creating a solid processed feedstock;
generating a primary syngas from the processed feedstock in a gasification unit;
generating superheated steam by cooling a stream comprising the primary syngas in a heat exchanger, thus outputting a cooled primary syngas stream;
generating electricity from the superheated steam;
removing or neutralizing one or more unwanted contaminants from the cooled primary syngas stream, thereby creating a scrubbed syngas;
compressing a compressor inlet stream comprising a first portion of the scrubbed syngas, thereby raising the pressure of the compressor inlet stream to a predefined level, and outputting a compressed syngas;
providing conditions within an alcohol synthesis reactor, including the presence of a catalyst, to cause components of at least a portion of the compressed syngas to react and produce an effluent comprising unconverted syngas and a mixture of reaction products including alcohols and water;
separating the effluent into a mixed-alcohol stream rich in water and alcohols, and one or more gas recycle streams rich in unconverted syngas; and
separating the mixed-alcohol stream into a number of streams comprising:
an ethanol stream comprising primarily ethanol;
a water stream comprising primarily water;
a methanol stream comprising primarily methanol; and
a heavy alcohol stream comprising primarily propanol and heavier alcohols;
conveying a methanol recycle stream comprising at least a portion of the methanol stream to a mixing point upstream of or within the alcohol synthesis reactor, thereby recycling the methanol recycle stream.

2. The method of claim 1, wherein the alcohol synthesis reactor comprises a first reaction zone, a second reaction zone in fluid communication with the first reaction zone, and
a space between the first reaction zone and the second reaction zone; and wherein said space comprises the mixing point.

3. The method of claim 2, wherein the first reaction zone and the second reaction zone are contained within separate reactor units.

4. The method of claim 1, wherein the methanol recycle stream is in the gas phase.

5. A method for converting organic materials into ethanol comprising:
separating non-organic materials from a solid feedstock which may optionally contain entrained liquids, thereby creating a solid processed feedstock;
generating a primary syngas from the processed feedstock in a gasification unit;
generating superheated steam by cooling a stream comprising the primary syngas in a heat exchanger, thus outputting a cooled primary syngas stream;

generating electricity from the superheated steam;

removing or neutralizing one or more unwanted contaminants from the cooled primary syngas stream, thereby creating a scrubbed syngas;

compressing a compressor inlet stream comprising a first portion of the scrubbed syngas, thereby raising the pressure of the compressor inlet stream to a predefined level, and outputting a compressed syngas;

providing conditions within an alcohol synthesis reactor, including the presence of a catalyst, to cause components of at least a portion of the compressed syngas to react and produce an effluent comprising unconverted syngas and a mixture of reaction products including alcohols and water;

separating the effluent into a mixed-alcohol stream rich in water and alcohols, and one or more gas recycle streams rich in unconverted syngas; and separating at least a portion of the mixed-alcohol stream into a number of streams comprising:
an ethanol stream comprising primarily ethanol;
a water stream comprising primarily water;
a methanol stream comprising primarily methanol; and
a heavy alcohol stream comprising primarily propanol and heavier alcohols;

conveying a fusel oil recycle stream comprising at least a portion of the heavy alcohol stream to the gasification unit;

within the gasification unit, partially oxidizing one or more components of the fusel oil recycle stream to convert at least some of said components to a mixture comprising carbon monoxide and hydrogen.

6. The method of claim 5, further comprising mixing a methyl acetate stream with the heavy alcohol stream, to create the fusel oil recycle stream.

7. The method of claim 6, further comprising:

separating said portion of the mixed alcohol stream into (A) a methanol-ethanol stream comprising methanol and ethanol, and (B) a heavies stream comprising propanol, other heavy alcohols, and water;

separating the heavies stream into (A) the heavy alcohol stream, and (B) the water stream;

separating the methanol-ethanol stream into (A) a methanol-methyl acetate stream comprising methanol and methyl acetate, and (B) the ethanol stream; and separating the methanol-methanol acetate stream into (A) the methyl acetate stream comprising methyl acetate, and (B) the methanol stream.

* * * * *